US009364525B2

(12) United States Patent
Cohen et al.

(10) Patent No.: US 9,364,525 B2
(45) Date of Patent: *Jun. 14, 2016

(54) VACCINES FOR MALARIA

(75) Inventors: Joseph D. Cohen, Rixensart (BE);
Martine Marchand, Rixensart (BE);
Christian F. Ockenhouse, Silver Spring, MD (US); Anjali Yadava, Silver Spring, MD (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 1382 days.

This patent is subject to a terminal disclaimer.

(21) Appl. No.: 12/374,238

(22) PCT Filed: Jul. 16, 2007

(86) PCT No.: PCT/EP2007/057296
§ 371 (c)(1),
(2), (4) Date: Feb. 16, 2010

(87) PCT Pub. No.: WO2008/009650
PCT Pub. Date: Jan. 24, 2008

(65) Prior Publication Data
US 2010/0150998 A1    Jun. 17, 2010

(30) Foreign Application Priority Data

| Jul. 18, 2006 | (GB) | 0614254.1 |
| Jul. 20, 2006 | (GB) | 0614473.7 |
| Jul. 20, 2006 | (GB) | 0614476.0 |
| Jul. 28, 2006 | (GB) | 0615115.3 |

(51) Int. Cl.
*A61K 39/015* (2006.01)
*A61K 39/00* (2006.01)
*C07K 14/445* (2006.01)
*C12N 7/00* (2006.01)

(52) U.S. Cl.
CPC ............ *A61K 39/015* (2013.01); *C07K 14/445* (2013.01); *A61K 2039/6075* (2013.01); *C07K 2319/40* (2013.01)

(58) Field of Classification Search
None
See application file for complete search history.

(56) References Cited

U.S. PATENT DOCUMENTS

| 4,235,877 | A  | 11/1980 | Fullerton et al. |
| 4,912,094 | A  | 3/1990  | Myers et al. |
| 4,997,647 | A  | 3/1991  | Nussenzweig et al. |
| 5,554,372 | A  | 9/1996  | Hunter |
| 5,666,153 | A  | 9/1997  | Copeland et al. |
| 6,083,716 | A  | 7/2000  | Wilson et al. |
| 6,303,347 | B1 | 10/2001 | Johnson et al. |
| 6,544,518 | B1 | 4/2003  | Friede et al. |
| 6,558,670 | B1 | 5/2003  | Friede et al. |
| 6,660,498 | B1 | 12/2003 | Hui et al. |
| 6,764,840 | B2 | 7/2004  | Johnson et al. |
| 7,790,186 | B2 * | 9/2010 | Yadava et al. ............... 424/268.1 |
| 8,999,347 | B2 * | 4/2015 | Cohen .................. A61K 39/015 424/185.1 |
| 2003/0133944 | A1 * | 7/2003 | Cohen ........................ 424/191.1 |
| 2004/0067236 | A1 | 4/2004 | Cohen et al. |
| 2006/0194196 | A1 | 8/2006 | Krupka et al. |
| 2008/0317787 | A1 | 12/2008 | Cohen |
| 2010/0210004 | A1 | 8/2010 | Kappe et al. |

FOREIGN PATENT DOCUMENTS

| EP | 0 362 278 | 12/1988 |
| EP | 0 109 942 | 5/1989 |
| EP | 0 468 520 | 1/1992 |
| EP | 0 671 948 B1 | 8/1997 |
| EP | 0 689 454 B1 | 9/1997 |
| EP | 1 623 720 A | 2/2006 |
| EP | 1 896 060 B1 | 12/2014 |
| GB | 2 220 211 A | 1/1990 |
| KR | 2000-0020497 | 4/2000 |
| WO | WO 93/10152 | 5/1993 |
| WO | WO 94/21292 | 9/1994 |
| WO | WO 95/26204 | 3/1995 |
| WO | WO 95/07353 | 5/1995 |
| WO | WO 95/14026 | 5/1995 |
| WO | WO 95/17210 | 6/1995 |
| WO | WO 96/33739 | 10/1996 |
| WO | WO 98/05355 | 2/1998 |
| WO | WO 98/15287 | 4/1998 |
| WO | WO 98/50399 | 11/1998 |
| WO | WO 98/56414 | 12/1998 |

(Continued)

OTHER PUBLICATIONS

McCutchan et al. Science 230: 1381-1383, 1985.*
pp. 65-70 of Evidence 1 as Common Knowledge, "High-tech approaches to the control of infections diseases", 1996, ISBN 7534520452 (CN Patent Application No. 200780034644 0).
Ballou, et al , "Safety and efficacy of a recombinant DNA plasmodium falciparum sporozoite vaccine" Lancet 1277 (1987).
Barr, et al, "Expression in Yeast of a Plasmodium Vivax Antigen of Potential Use in a Human Malaria Vaccine", Journal Exp Med , vol. 165, 1160, 1987.

(Continued)

*Primary Examiner* — S. Devi
(74) *Attorney, Agent, or Firm* — Virginia G. Campen

(57) ABSTRACT

The present invention relates to a novel lipoprotein particle, methods for preparing and purifying the same, its use in medicine, particularly in the prevention of malarial infections, compositions/vaccines containing the particle or antibodies against the protein particle such as monoclonal or polyclonal antibodies and use of the same, particularly in therapy. In particular it relates to an immunogenic protein particle comprising the following monomers:
  a. a fusion protein comprising sequences derived from a CS protein of *P. vivax* and the S antigen of Hepatitis B (CSV-S), and
  b. a fusion protein comprising sequences derived from CS protein of *P. falciparum* and S antigen of Hepatitis B (RTS), and
  c. optionally the S antigen derived from Hepatitis B.

13 Claims, 8 Drawing Sheets

(56) References Cited

FOREIGN PATENT DOCUMENTS

| | | |
|---|---|---|
| WO | WO 01/46127 | 12/1999 |
| WO | WO 00/00462 | 1/2000 |
| WO | WO 02/13765 | 2/2002 |
| WO | WO 02/36792 | 5/2002 |
| WO | WO 03/000283 | 1/2003 |
| WO | WO 2004/037189 | 5/2004 |
| WO | WO 2004/055187 | 7/2004 |
| WO | WO 2004/113369 | 12/2004 |
| WO | WO 2005/001103 | 1/2005 |
| WO | WO 2005/025614 | 3/2005 |
| WO | WO2006/029887 | 3/2006 |

OTHER PUBLICATIONS

Bett, et al , "Packaging capacity and stability of human adenovirus Type 5 vectors", J Virol 67 (10), 5911-21 (1993).

Broach, et al , "Transformation in Yeast Development of a Hybrid Cloning Vector and Isolation of the CAN 1 Gene", Gene 8 121-133, (1979).

Chitnis, et al , "Targeting the Plasmodium vivax Duffy-binding protein", Trends in Parasitology, 24(1) 29-34 (2007).

Clyde, "Immunization of man against falciparum and vivax malaria by uses of attenuated sporozoites", Am J, Trop Med Hyg 24 397-402, (1975).

Collins, et al , "Immunization of *Saimin Sciureus Boliviensis* with recombinant vaccines based on the circumsporozoite protein of *Plasmodium Vivax*", Am J Trop Med Hyg 40, 455-64 (1989).

Dalsgaard et al in 1974 ("Saponin adjuvants", Archly fur die gesamte Virusforschung, vol. 44, Springer Verlag, Berlin, 243-254).

Dame, et al , "Structure of the Gene Encoding the Immunodominant Surface Antigen on the Sporozoites of the Human Malaria Parasite Plasmodium falciparum", Science 225 593-599, (1984).

Fitzgerald, et al , "A Simian Replication-Defective Adenoviral Recombinant Vaccine to HIV-1 Gag", J Immunol 170 1416 (2003).

Gantt, et al, "Cell Adhesion to a Motif Shared by the Malaria Circumsporozoite Protein and Thrombospondin is Mediated by Its Glycosaminoglycan-binding region and not by CSVTCG", TheJournal of Biological Chemistry, 272(31) 19205-19213 (1977).

Harford, et al , "Construction and Characterization of a *Saccharomyces cerevisiae* Strain (RIT4376) Expressing Hepatitis B Surface Antigen", Postgrad Med J 63, Supp 2 65-70, (1987).

Heppner et al , Towards an RTS,S-based, multi-stage, multi-antigen vaccine against falciparum malaria progress at the Walter Reed Army Institute of Research, Vaccine 23, 2243-50 (2005).

Herrington, et al , "Safety and immunogenicity in man of a synthetic peptide malaria vaccine against *Plasmodium falciparum* sporozoites", Nature 328 257 (1987).

Hinnen , et al , "Transformation of Yeast", Proc Natl Acad Sci USA 75 1929-1933, (1980).

Illustrated Stedman's Medical Dicitonary, 24$^{th}$ Edition, Williams nad Wilkins, London, p. 707 (1982).

Jacobs, et al , "Simultaneous Synthesis and Assembly of Various Hepatitis B Surface Proteins in *Saccharomyces cerevisiae*", Gene 80 279-291, (1989).

Martinez, et al , "Plasmodium vivax Duffy binding protein a modular revolutionary proposal" Parasitology, 128, 353-366 (2004).

Miller, "Erythrocyte receptors for (Plasmodium knowlesi) Malaria Duffy blood group determinants", Science, 189(4202) 561-563 (1975).

Nardelli, et al , "The MAP System A flexible and unambiguous vaccine design of branched peptides", Pharm Biotechnol 6, 803-19 (1995).

New Riverside University Dictionary The Riverside Publishing Company, p. 933 (1984).

Oxford Dictionary of Biochemistry and Molecular Biology, Oxford University Press, p. 81 (2003).

Parks, et al , "A Helper-Dependent System for Adenovirus Vector Production Helps Define a Lower Limit for Efficient DNA Packaging", J Virol 71(4), 3293-8 (1997).

Qari, et al , Wide distribution of the variant form of the human malaria parasite *Plasmodium vivax*, JournalOfBiolChem 266(25) 16297, 1991.

Rathore, et al , "Binding and Invasion of Liver Cells by Plasmodium falciparum Sporozoites", J Biol Chem 277(9) 7092-7098, (2002).

Roy et al , "Characterization of a Family of Chimpanzee Adenoviruses and Development of Molecular Clones for Gene Transfer Vectors" Human Gene Therapy 15 519-530 (2004).

Russell W C , "Update on adenovirus and its vectors", Gen Viriol, 81 2573-2604 (2000).

Schodel, et al , "Hybrid hepatitis B virus core antigen as a vaccine carrier moiety I Presentation of foreign epitopes", Journal of Biotechnology, 44 91-96 (1996).

Suh, et al , "Comparison of Immunological Responses to Various Types of Circumsporozoite Proteins of Plasmodium vivax in Malaria Patients of Korea", Microbial Immunol 48(2) 119-123, Microbiol Immunol 2004, 48(2) 119-123 (2004).

Sun, et al , "Protective Immunity Induced with Malaria Vaccine, RTS,S, Is Linked to *Plasmodium falciparum* Circumsporozoite Protein-Specific CD4+ and CD8+ T Cells Producing IFNγ1", *The Journal of Immunology*, 171 6961-6967 (2003).

Thomas, et al , "Inducing a Cell-Mediated Immune Response Against Peptides of the Plasmodium Vivax Circumsporozoite Protein", *Annals of Tropical Medicine and Parasitology*, 95 6, 573-586 (Sep. 2001).

Valenzuela, et al , "Nucleotide sequence of the gene coding for the major protein of hepatitis B virus surface antigen", Nature 280 815-819 (1979).

Venkatachalam, et al , "Immunogenicity of Plasmodium Falciparum and Plasmodium Vivax Circumsporozoite Protein Repeat Multiple Antigen Constructs (MAC)", *Vaccine*, 16 9-10, 982-988 (May 1998).

Vieira, et al , "The pUC plasmids, an M13mp7-Derived System for Insertion Mutagenesis and Sequencing with Synthetic Universal Primers", Gene 19 259-268, (1982).

Zhang, et al , "Double Stranded SDNA Sequencing as a Choice for DNA Sequencing", Nucleic Acids Research 16 1220, (1988).

* cited by examiner

Plasmid map of pRIT15546

Figure 3: Plasmid map of pRIT15582.
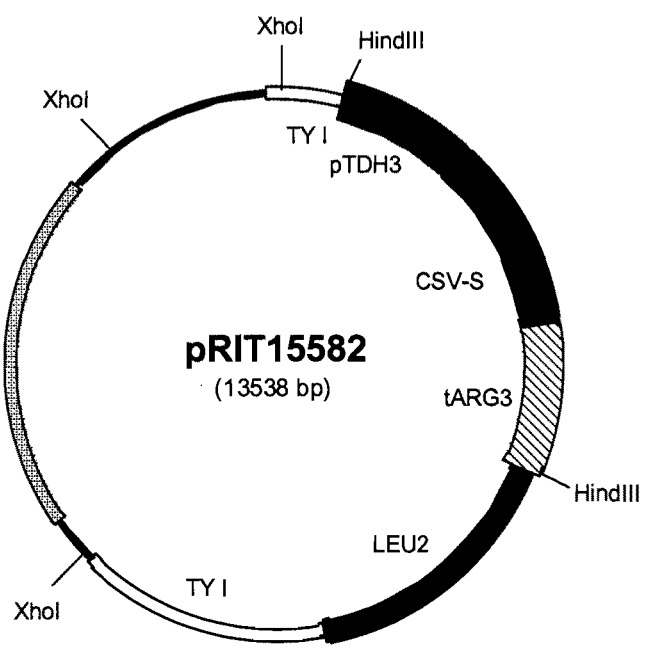

Figure 4: Restriction map of the linear XhoI fragment used to integrate CSV-S cassette.

Figure 5: Western blot of recombinant proteins expressed in strain Y1835.
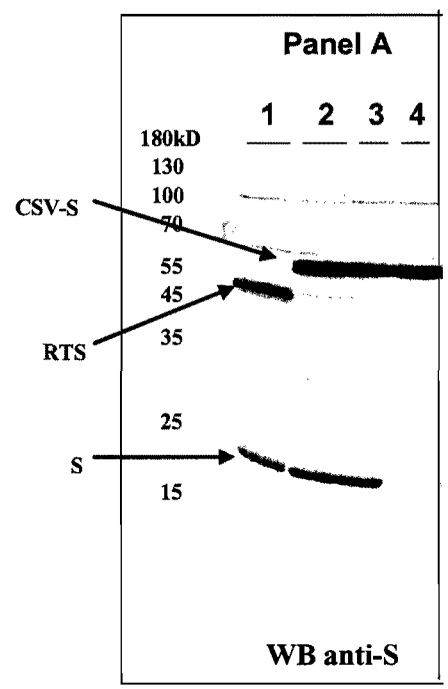
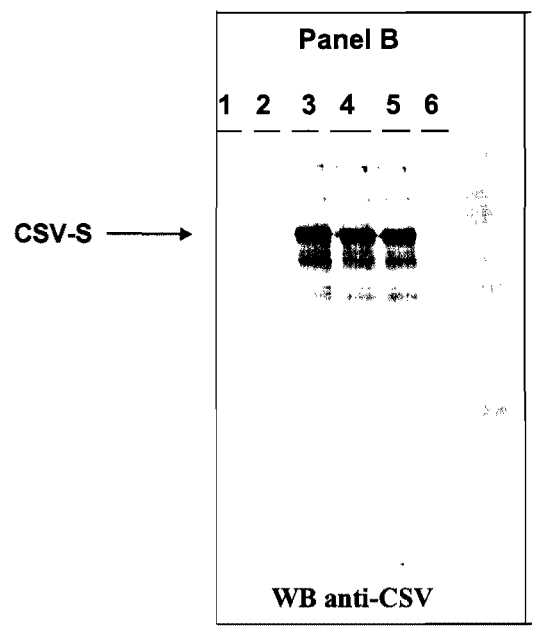

Figure 6: Electron micrograph of CSV-S,S mixed particles produced in strain Y1835

Figure 7: Western blot of recombinant proteins expressed in strain Y1845.

Figure 8: CsCl density analysis of a cell-free extract prepared from strain Y1845.
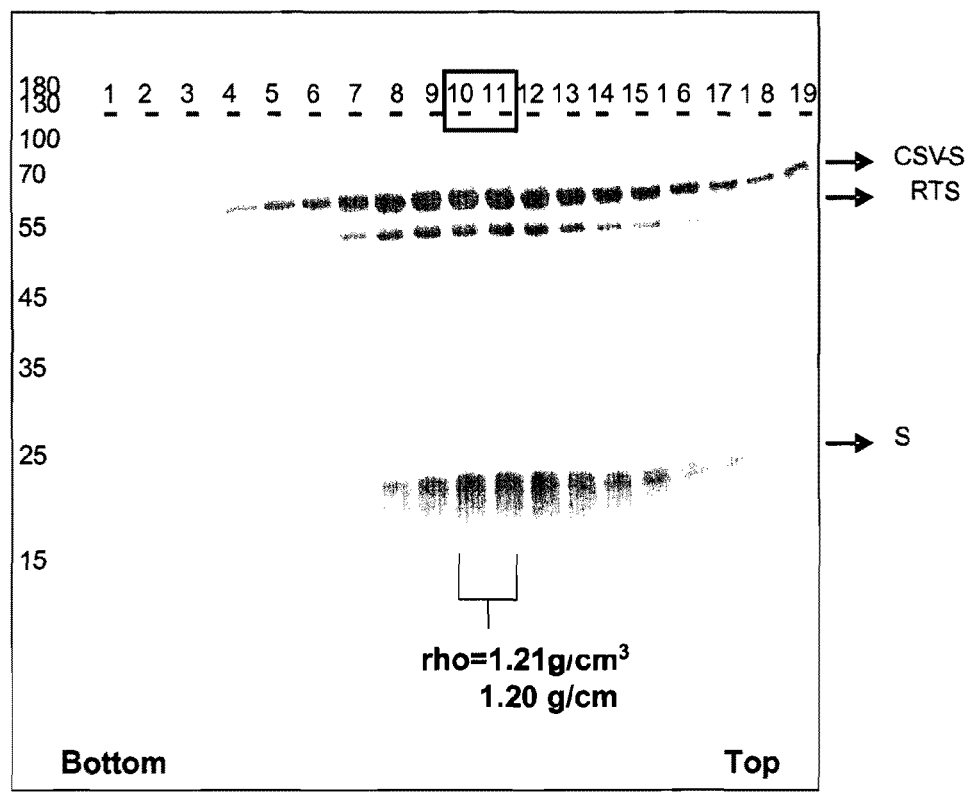

SEQUENCE LISTING

```
<160> NUMBER OF SEQ ID NOS: 27

<210> SEQ ID NO 1
<211> LENGTH: 5
<212> TYPE: PRT
<213> ORGANISM: Plasmodium Vivax

<400> SEQUENCE: 1

Lys Leu Lys Gln Pro
 1               5

<210> SEQ ID NO 2
<211> LENGTH: 6
<212> TYPE: PRT
<213> ORGANISM: Plasmodium Vivax

<400> SEQUENCE: 2

Cys Ser Val Thr Cys Gly
 1               5

<210> SEQ ID NO 3
<211> LENGTH: 9
<212> TYPE: PRT
<213> ORGANISM: Plasmodium Vivax

<400> SEQUENCE: 3

Gly Asp Arg Ala Ala Gly Gln Pro Ala
 1               5

<210> SEQ ID NO 4
<211> LENGTH: 9
<212> TYPE: PRT
<213> ORGANISM: Plasmodium Vivax

<400> SEQUENCE: 4

Gly Asp Arg Ala Asp Gly Gln Pro Ala
 1               5

<210> SEQ ID NO 5
<211> LENGTH: 9
<212> TYPE: PRT
<213> ORGANISM: Plasmodium Vivax

<400> SEQUENCE: 5

Gly Asp Arg Ala Asp Gly Gln Ala Ala
 1               5

<210> SEQ ID NO 6
<211> LENGTH: 9
<212> TYPE: PRT
<213> ORGANISM: Plasmodium Vivax

<400> SEQUENCE: 6

Gly Asn Gly Ala Gly Gly Gln Pro Ala
 1               5
```

```
<210> SEQ ID NO 7
<211> LENGTH: 9
<212> TYPE: PRT
<213> ORGANISM: Plasmodium Vivax

<400> SEQUENCE: 7

Gly Asp Gly Ala Ala Gly Gln Pro Ala
 1               5

<210> SEQ ID NO 8
<211> LENGTH: 9
<212> TYPE: PRT
<213> ORGANISM: Plasmodium Vivax

<400> SEQUENCE: 8

Gly Asp Arg Ala Ala Gly Gln Ala Ala
 1               5

<210> SEQ ID NO 9
<211> LENGTH: 9
<212> TYPE: PRT
<213> ORGANISM: Plasmodium Vivax

<400> SEQUENCE: 9

Gly Asn Gly Ala Gly Gly Gln Ala Ala
 1               5

<210> SEQ ID NO 10
<211> LENGTH: 9
<212> TYPE: PRT
<213> ORGANISM: Plasmodium Vivax

<400> SEQUENCE: 10

Ala Asn Gly Ala Gly Asn Gln Pro Gly
 1               5

<210> SEQ ID NO 11
<211> LENGTH: 12
<212> TYPE: PRT
<213> ORGANISM: Plasmodium Vivax

<400> SEQUENCE: 11

Gly Gly Asn Ala Ala Asn Lys Lys Ala Glu Asp Ala
 1               5                  10

<210> SEQ ID NO 12
<211> LENGTH: 771
<212> TYPE: DNA
<213> ORGANISM: Artificial Sequence
<220> FEATURE:
<223> OTHER INFORMATION: Nucleotide sequence for a hybrid
      circumsporozite protein derived from different types of Plasmodium
      Vivax (codon optimized for expression in E. coli)

<400> SEQUENCE: 12
acacattgcg gacataatgt agatttatct aaagctataa atttaaatgg tgtaaacttc      60
aataacgtag acgctagttc actcggggct gcgcacgtag gtcagtctgc tagcagggg     120 cgcggtctcg ggaaaaaccc agacgacgaa gaaggtgatg ctaaaaagaa aaaggacggt    180
aaaaaagcgg aaccaaaaaa tccaagggaa aataaattaa acagcccgg ggatcgcgcg    240 gatggtcaag cggcgggtaa tggggcgggg ggtcaaccag cggggatcg cgcggctggt    300 cagccagcgg gggatcgcgc ggctggtcag ccagcgggg atggtgcggc tggccaacca    360
gcgggggatc gcgcggatgg tcagccagcg ggggatcgcg cggatggtca accagccgt    420
```

```
gatcgcgcgg ctggccaagc ggccggtaat ggggcggggg gtcaagcggc cgcgaacgga      480
gcggggaacc agccaggcgg cggtaacgct gcgaataaaa aagcggaaga tgcgggtggt      540
aacgcgggcg gtaatgcggg cggccaaggt cagaacaacg aagggctaa tgcaccaaac      600 gaaaaatctg tcaaagaata tctcgataaa gtccgcgcta cagtagggac agaatggacg      660
ccatgctctg taacatgtgg tgtcggggta cgcgtgcgcc gccgtgtcaa tgcggctaac      720
aaaaaaccag aagatctcac gttaaatgat ctcgaaacgg atgtctgcac a              771
```

<210> SEQ ID NO 13
<211> LENGTH: 257
<212> TYPE: PRT
<213> ORGANISM: Artificial Sequence
<220> FEATURE:
<223> OTHER INFORMATION: Amino acid sequence for a hybrid
     circumsporozite protein derived from different types of Plasmodium
     Vivax

<400> SEQUENCE: 13

Thr His Cys Gly His Asn Val Asp Leu Ser Lys Ala Ile Asn Leu Asn
1               5                   10                  15

Gly Val Asn Phe Asn Asn Val Asp Ala Ser Ser Leu Gly Ala Ala His
            20                  25                  30

Val Gly Gln Ser Ala Ser Arg Gly Arg Gly Leu Gly Glu Asn Pro Asp
        35                  40                  45

Asp Glu Glu Gly Asp Ala Lys Lys Lys Asp Gly Lys Lys Ala Glu
    50                  55                  60

Pro Lys Asn Pro Arg Glu Asn Lys Leu Lys Gln Pro Gly Asp Arg Ala
65                  70                  75                  80

Asp Gly Gln Ala Ala Gly Asn Gly Ala Gly Gly Gln Pro Ala Gly Asp
                85                  90                  95

Arg Ala Ala Gly Gln Pro Ala Gly Asp Arg Ala Ala Gly Gln Pro Ala
            100                 105                 110

Gly Asp Gly Ala Ala Gly Gln Pro Ala Gly Asp Arg Ala Asp Gly Gln
        115                 120                 125

Pro Ala Gly Asp Arg Ala Asp Gly Gln Pro Ala Gly Asp Arg Ala Ala
    130                 135                 140

Gly Gln Ala Ala Gly Asn Gly Ala Gly Gly Ala Ala Ala Asn Gly
145                 150                 155                 160

Ala Gly Asn Gln Pro Gly Gly Gly Asn Ala Ala Asn Lys Lys Ala Glu
                165                 170                 175

Asp Ala Gly Gly Asn Ala Gly Gly Asn Ala Gly Gly Gln Gly Gln Asn
            180                 185                 190

Asn Glu Gly Ala Asn Ala Pro Asn Glu Lys Ser Val Lys Glu Tyr Leu
        195                 200                 205

Asp Lys Val Arg Ala Thr Val Gly Thr Glu Trp Thr Pro Cys Ser Val
    210                 215                 220

Thr Cys Gly Val Gly Val Arg Val Arg Arg Val Asn Ala Ala Asn
225                 230                 235                 240

Lys Lys Pro Glu Asp Leu Thr Leu Asn Asp Leu Glu Thr Asp Val Cys
                245                 250                 255

Thr

<210> SEQ ID NO 14
<211> LENGTH: 9
<212> TYPE: PRT

<213> ORGANISM: Plasmodium Vivax

<400> SEQUENCE: 14

Ala Asn Gly Ala Gly Asp Gln Pro Gly
 1               5

<210> SEQ ID NO 15
<211> LENGTH: 771
<212> TYPE: DNA
<213> ORGANISM: Artificial Sequence
<220> FEATURE:
<223> OTHER INFORMATION: Nucleotide sequence for a hybrid
      circumsporozite protein derived from different types of Plasmodium
      Vivax (codon optimized for expression in yeast)

<400> SEQUENCE: 15

```
acccattgtg gtcacaatgt cgatttgtct aaggccatta acttgaacgg tgttaatttc      60
aacaacgtcg atgcttcttc tttaggtgcc gctcatgttg gtcaatctgc ttcaagaggt     120
agaggtttag gtgaaaaccc agacgacgaa gaaggtgacg ctaagaagaa gaaggacggt     180
aagaaggccg aaccaaagaa cccaagagaa acaagttgaa caaccagg tgacagagcc      240
gacggacaag cagctggtaa tggtgctgga ggtcaaccag ctggtgacag agctgccggt     300
cagcctgctg gtgatagagc tgctggacaa cctgctggag acggtgccgc cggtcaacct     360
gctggtgata gagcagacgg acaaccagct ggtgaccgtg ctgacggaca gccagccggc     420
gatagggctg caggtcaagc cgctggtaac ggtgccggtg gtcaagctgc tgctaacggt     480
gctggtaacc aaccaggtgg tggtaacgct gccaacaaga aagctgaaga cgctggtggt     540
aatgctggag gtaatgcagg tggtcagggt caaaacaacg aaggtgctaa cgctccaaac     600
gaaaagtctg ttaaggaata cttagataag gttagagcta ctgtcggtac tgaatggact     660
ccatgttctg ttacttgtgg tgtcggtgtt agagttagaa gaagagttaa cgccgctaac     720
aagaagccag aagacttgac tctaaacgac ttggaaactg acgtttgtac t              771
```

<210> SEQ ID NO 16
<211> LENGTH: 1485
<212> TYPE: DNA
<213> ORGANISM: Artificial Sequence
<220> FEATURE:
<223> OTHER INFORMATION: Nucleotide sequence for a hybrid fusion protein
      (CSV-S) of circumsporozite protein derived from
      different types of Plasmodium Vivax and the S
      antigen from Hepatitis B

<400> SEQUENCE: 16

```
atgatggctc ccgggaccca ttgtggtcac aatgtcgatt tgtctaaggc cattaacttg      60
aacggtgtta atttcaacaa cgtcgatgct tcttctttag gtgccgctca tgttggtcaa     120
tctgcttcaa gaggtagagg tttaggtgaa aacccagacg acgaagaagg tgacgctaag     180
aagaagaagg acgtaagaa ggccgaacca agaacccaa gagaaacaa gttgaaacaa       240
ccaggtgaca gagccgacgg acaagcagct ggtaatggtg ctggaggtca accagctggt     300
gacagagctg ccggtcagcc tgctggtgat agagctgctg acaacctgc tggagacggt      360
gccgccggtc aacctgctgg tgatagagca acggacaac cagctggtga ccgtgctgac      420
ggacagccag ccggcgatag ggctgcaggt caagccgctg gtaacggtgc cggtggtcaa     480
gctgctgcta acggtgctgg taaccaacca ggtggtggta acgctgccaa caagaaagct     540
gaagacgctg gtggtaatgc tggaggtaat gcaggtggtc agggtcaaaa caacgaaggt     600
gctaacgctc caaacgaaaa gtctgttaag gaatacttag ataaggttag agctactgtc     660
```

```
ggtactgaat ggactccatg ttctgttact tgtggtgtcg gtgttagagt tagaagaaga    720
gttaacgccg ctaacaagaa gccagaagac ttgactctaa cgacttgga aactgacgtt    780 tgtactcccg ggcctgtgac gaacatggag aacatcacat caggattcct aggacccctg    840
ctcgtgttac aggcgggtt tttcttgttg acaagaatcc tcacaatacc gcagagtcta    900
gactcgtggt ggacttctct caatttcta ggggatcac ccgtgtgtct tggccaaaat    960
tcgcagtccc caacctccaa tcactcacca acctcctgtc ctccaatttg tcctggttat   1020
cgctggatgt gtctgcggcg ttttatcata ttcctcttca tcctgctgct atgcctcatc   1080
ttcttattgg ttcttctgga ttatcaaggt atgttgcccg tttgtcctct aattccagga   1140
tcaacaacaa ccaatacggg accatgcaaa acctgcacga ctcctgctca aggcaactct   1200
atgtttccct catgttgctg tacaaaacct acggatggaa attgcacctg tattcccatc   1260
ccatcgtcct gggctttcgc aaaatacctA tgggagtggg cctcagtccg tttctcttgg   1320
ctcagtttac tagtgccatt tgttcagtgg ttcgtagggc tttcccccac tgtttggctt   1380
tcagctatat ggatgatgtg gtattgggg ccaagtctgt acagcatcgt gagtcccttt   1440
ataccgctgt taccaatttt cttttgtctc tgggtataca tttaa                  1485
```

<210> SEQ ID NO 17
<211> LENGTH: 494
<212> TYPE: PRT
<213> ORGANISM: Artificial Sequence
<220> FEATURE:
<223> OTHER INFORMATION: Amino acid sequence for a hybrid fusion protein (CSV-S) of circumsporozite protein derived from different types of Plasmodium Vivax and the S antigen from Hepatitis B

<400> SEQUENCE: 17

```
Met Met Ala Pro Gly Thr His Cys Gly His Asn Val Asp Leu Ser Lys
  1               5                  10                  15

Ala Ile Asn Leu Asn Gly Val Asn Phe Asn Asn Val Asp Ala Ser Ser
                 20                  25                  30

Leu Gly Ala Ala His Val Gly Gln Ser Ala Ser Arg Gly Arg Gly Leu
             35                  40                  45

Gly Glu Asn Pro Asp Asp Glu Glu Gly Asp Ala Lys Lys Lys Lys Asp
         50                  55                  60

Gly Lys Lys Ala Glu Pro Lys Asn Pro Arg Glu Asn Lys Leu Lys Gln
 65                  70                  75                  80

Pro Gly Asp Arg Ala Asp Gly Gln Ala Ala Gly Asn Gly Ala Gly Gly
                 85                  90                  95

Gln Pro Ala Gly Asp Arg Ala Ala Gly Gln Pro Ala Gly Asp Arg Ala
            100                 105                 110

Ala Gly Gln Pro Ala Gly Asp Gly Ala Ala Gly Gln Pro Ala Gly Asp
            115                 120                 125

Arg Ala Asp Gly Gln Pro Ala Gly Asp Arg Ala Asp Gly Gln Pro Ala
        130                 135                 140

Gly Asp Arg Ala Ala Gly Gln Ala Ala Gly Asn Gly Ala Gly Gly Gln
145                 150                 155                 160

Ala Ala Ala Asn Gly Ala Gly Asn Gln Pro Gly Gly Asn Ala Ala
                165                 170                 175

Asn Lys Lys Ala Glu Asp Ala Gly Gly Asn Ala Gly Gly Asn Ala Gly
            180                 185                 190

Gly Gln Gly Gln Asn Asn Glu Gly Ala Asn Ala Pro Asn Glu Lys Ser
```

```
                195                 200                 205
Val Lys Glu Tyr Leu Asp Lys Val Arg Ala Thr Val Gly Thr Glu Trp
    210                 215                 220

Thr Pro Cys Ser Val Thr Cys Gly Val Gly Val Arg Val Arg Arg Arg
225                 230                 235                 240

Val Asn Ala Ala Asn Lys Lys Pro Glu Asp Leu Thr Leu Asn Asp Leu
                245                 250                 255

Glu Thr Asp Val Cys Thr Pro Gly Pro Val Thr Asn Met Glu Asn Ile
            260                 265                 270

Thr Ser Gly Phe Leu Gly Pro Leu Leu Val Leu Gln Ala Gly Phe Phe
        275                 280                 285

Leu Leu Thr Arg Ile Leu Thr Ile Pro Gln Ser Leu Asp Ser Trp Trp
    290                 295                 300

Thr Ser Leu Asn Phe Leu Gly Gly Ser Pro Val Cys Leu Gly Gln Asn
305                 310                 315                 320

Ser Gln Ser Pro Thr Ser Asn His Ser Pro Thr Ser Cys Pro Pro Ile
                325                 330                 335

Cys Pro Gly Tyr Arg Trp Met Cys Leu Arg Arg Phe Ile Ile Phe Leu
            340                 345                 350

Phe Ile Leu Leu Leu Cys Leu Ile Phe Leu Leu Val Leu Leu Asp Tyr
        355                 360                 365

Gln Gly Met Leu Pro Val Cys Pro Leu Ile Pro Gly Ser Thr Thr Thr
    370                 375                 380

Asn Thr Gly Pro Cys Lys Thr Cys Thr Thr Pro Ala Gln Gly Asn Ser
385                 390                 395                 400

Met Phe Pro Ser Cys Cys Cys Thr Lys Pro Thr Asp Gly Asn Cys Thr
                405                 410                 415

Cys Ile Pro Ile Pro Ser Ser Trp Ala Phe Ala Lys Tyr Leu Trp Glu
            420                 425                 430

Trp Ala Ser Val Arg Phe Ser Trp Leu Ser Leu Leu Val Pro Phe Val
        435                 440                 445

Gln Trp Phe Val Gly Leu Ser Pro Thr Val Trp Leu Ser Ala Ile Trp
    450                 455                 460

Met Met Trp Tyr Trp Gly Pro Ser Leu Tyr Ser Ile Val Ser Pro Phe
465                 470                 475                 480

Ile Pro Leu Leu Pro Ile Phe Phe Cys Leu Trp Val Tyr Ile
                485                 490

<210> SEQ ID NO 18
<211> LENGTH: 3509
<212> TYPE: DNA
<213> ORGANISM: Artificial Sequence
<220> FEATURE:
<223> OTHER INFORMATION: Nucleotide sequence for a hybrid fusion protein
      (RTS) of circumsporozite protein of Plasmodium
      Falciparum and the S antigen from Hepatitis B

<400> SEQUENCE: 18
aagcttacca gttctcacac ggaacaccac taatggacac aaattcgaaa tactttgacc    60
ctattttcga ggaccttgtc accttgagcc caagagagcc aagatttaaa ttttcctatg   120
acttgatgca aattcccaaa gctaataaca tgcaagacac gtacggtcaa gaagacatat   180
ttgacctctt aactggttca gacgcgactg cctcatcagt aagacccgtt gaaagaact    240 tacctgaaaa aaacgaatat atactagcgt tgatgttag cgtcaacaac aagaagttta   300
atgacgcgga ggccaaggca aaaagattcc ttgattacgt aagggagtta gaatcatttt   360
```

```
gaataaaaaa cacgcttttt cagttcgagt ttatcattat caatactgcc atttcaaaga    420
atacgtaaat aattaatagt agtgattttc ctaactttat ttagtcaaaa attagccttt    480
taattctgct gtaacccgta catgcccaaa ataggggggcg ggttacacag aatatataac   540
atcgtaggtg tctgggtgaa cagtttatcc ctggcatcca ctaaatataa tggagctcgc    600
ttttaagctg gcatccagaa aaaaaagaa tcccagcacc aaaatattgt tttcttcacc     660
aaccatcagt tcataggtcc attctcttag cgcaactaca gagaacaggg gcacaaacag    720
gcaaaaaacg ggcacaacct caatggagtg atgcaacctg cctggagtaa atgatgacac    780
aaggcaattg acccacgcat gtatctatct cattttctta caccttctat taccttctgc    840
tctctctgat ttggaaaaag ctgaaaaaaa aggttgaaac cagttccctg aaattattcc    900
cctacttgac taataagtat ataaagacgg taggtattga ttgtaattct gtaaatctgt    960
aaatctattt cttaaacttc ttaaattcta cttttatagt tagtcttttt tttagttttta  1020 aaacaccaag aacttagttt cgaataaaca cacataaaca aacaaaatga tggctcccga   1080
tcctaatgca aatccaaatg caaacccaaa tgcaaaccca aacgcaaacc ccaatgcaaa   1140
tcctaatgca aaccccaatg caaatcctaa tgccaatcct aatgccaatc caaatgcaaa   1200
tccaaatgca aacccaaacg caaaccccaa tgcaaatcct aatgccaatc caaatgcaaa   1260
tccaaatgca aacccaaatg caaacccaaa tgcaaacccc aatgcaaatc ctaataaaaa   1320
caatcaaggt aatggacaag gtcacaatat gccaaatgac ccaaaccgaa atgtagatga   1380
aaatgctaat gccaacaatg ctgtaaaaaa taataataac gaagaaccaa gtgataagca   1440
catagaacaa tatttaaaga aaataaaaaa ttctatttca actgaatggt ccccatgtag   1500
tgtaacttgt ggaaatggta ttcaagttag aataaagcct ggctctgcta ataaacctaa   1560
agacgaatta gattatgaaa atgatattga aaaaaaaatt tgtaaaatgg aaaagtgctc   1620
gagtgtgttt aatgtcgtaa atagtcgacc tgtgacgaac atggagaaca tcacatcagg   1680
attcctagga cccctgctcg tgttacaggc ggggttttc ttgttgacaa gaatcctcac    1740
aataccgcag agtctagact cgtggtggac ttctctcaat tttctagggg gatcacccgt   1800
gtgtcttggc caaaattcgc agtccccaac ctccaatcac tcaccaacct cctgtcctcc   1860
aatttgtcct ggttatcgct ggatgtgtct gcgcgtttta tcatattcct cttcatcctg   1920
ctgctatgcc tcatcttctt attggttctt ctggattatc aaggtatgtt gcccgtttgt   1980
cctctaattc caggatcaac aacaaccaat acgggaccat gcaaaacctg cacgactcct   2040
gctcaaggca actctatgtt tccctcatgt tgctgtacaa aacctacgga tggaaattgc    2100
acctgtattc ccatcccatc gtcctgggct ttcgcaaaat acctatggga gtgggcctca    2160
gtccgtttct cttggctcag tttactagtg ccatttgttc agtggttcgt agggcttttcc   2220 cccactgttt ggctttcagc tatatggatg atgtggtatt gggggccaag tctgtacagc    2280
atcgtgagtc cctttatacc gctgttacca attttctttt gtctctgggt atacatttaa    2340
cgaattccaa gctgaaacaa ttcaaaggtt ttcaaatcaa tcaagaactt gtctctgtgg    2400
ctgatccaaa ctacaaattt atgcattgtc tgccaagaca tcaagaagaa gttagtgatg    2460 atgtcttta tggagagcat tccatagtct ttgaagaagc agaaaacaga ttatatgcag     2520
ctatgtctgc cattgatatc tttgttaata ataaaggtaa tttcaaggac ttgaaataat    2580
ccttctttcg tgttcttaat aactaatata taaatacaga tatagatgca tgaataatga    2640
tatacattga ttattttgca atgtcaatta aaaaaaaaaa atgttagtaa aactatgtta    2700
```

| | | |
|---|---|---|
| cattccaagc aaataaagca cttggttaaa cgaaattaac gttttttaaga cagccagacc | 2760 |
| gcggtctaaa aatttaaata tacactgcca acaaattcct tcgagttgtc caatttcacc | 2820 |
| actttatat tttcatcaac ttcagcagat tcaaccttct cacatagaac attggaataa | 2880 |
| acagccttaa caccactttc aagtttgcac agcgtaatat gaggaatttt gttttgacaa | 2940 |
| cacaacccctt taattttctc attgttttca tcaattatgc atccatcttt atctttagac | 3000 |
| agttccacta caatagcaat agttttttca tcccaacata gttttcgag cctaaaattc | 3060 |
| agtttgtcgg tcgtttacc tgcgtatttt ggttattacc agagccttgt gcattttcta | 3120 |
| tgcggttgtt attgtactcc gttatctggt cagtgtatct gttacaatat gattccacaa | 3180 |
| ctttttgcc tcttttcac gggacgacat gacatgacct aatgttatat gaagttcctt | 3240 |
| ctgaactttt ccactagcta gtaaatgctt gaatttctca gtcagctctg catcgctagc | 3300 |
| aatacacctc ttgaccaatc aataatttca tcgtagtttt ctatttagct gagatatatg | 3360 |
| taggtttaat taacttagcg ttttttgttg attattgttg cctttaccaa ctatttttct | 3420 |
| cacagtaggt ttgtaatcta agctccttct gaacgctgtc tcaatttcat catctttcgg | 3480 |
| gatctctggt accaaaattg gataagctt | 3509 |

<210> SEQ ID NO 19
<211> LENGTH: 445
<212> TYPE: PRT
<213> ORGANISM: Artificial Sequence
<220> FEATURE:
<223> OTHER INFORMATION: Amino acid sequence for a hybrid fusion protein (RTS) of circumsporozite protein of Plasmodium Falciparum and the S antigen from Hepatitis B

<400> SEQUENCE: 19

```
Met Met Ala Pro Asp Pro Asn Ala Leu Asn Pro Asn Ala Asn Pro Asn
  1               5                   10                  15
Ala Asn Pro Asn Ala Asn Pro Asn Ala Asn Pro Asn Ala Leu Asn Pro
             20                  25                  30
Asn Ala Asn Pro Asn Ala Asn Pro Asn Ala Asn Pro Asn Ala Asn Pro
         35                  40                  45
Asn Ala Leu Asn Pro Asn Ala Asn Pro Asn Ala Asn Pro Asn Ala Asn
     50                  55                  60
Pro Asn Ala Asn Pro Asn Leu Asn Pro Asn Ala Asn Pro Asn Ala Asn
 65                  70                  75                  80
Pro Asn Ala Asn Pro Asn Lys Asn Asn Gln Gly Leu Asn Gly Gln Gly
                 85                  90                  95
His Asn Met Pro Asn Asp Pro Asn Asp Pro Asn Arg Asn Val Asp Glu
                100                 105                 110
Asn Ala Asn Ala Asn Asn Ala Val Lys Asn Asn Asn Glu Glu Pro
            115                 120                 125
Ser Asp Lys His Ile Glu Gly Leu Tyr Leu Lys Lys Ile Lys Asn Ser
        130                 135                 140
Ile Ser Thr Glu Trp Ser Pro Cys Ser Val Thr Cys Tyr Gly Asn Gly
145                 150                 155                 160
Ile Gln Val Arg Ile Lys Pro Gly Ser Ala Asn Lys Pro Lys Asp Glu
                165                 170                 175
Leu Asp Tyr Glu Asn Asp Ile Glu Lys Lys Ile Cys Lys Met Glu Lys
                180                 185                 190
Cys Ser Ser Val Pro His Asn Val Val Asn Ser Arg Pro Val Thr Asn
            195                 200                 205
```

```
Met Glu Asn Ile Thr Ser Gly Phe Leu Gly Leu Pro Leu Val Leu
210                 215                 220

Gln Ala Gly Phe Phe Leu Leu Thr Arg Ile Leu Thr Ile Pro Gly Leu
225                 230                 235                 240

Ser Leu Asp Ser Trp Trp Thr Ser Leu Asn Phe Leu Gly Gly Ser Pro
                245                 250                 255

Val Cys Leu Gly Leu Gln Asn Ser Gln Ser Pro Thr Ser Asn His Ser
                260                 265                 270

Pro Thr Ser Cys Pro Pro Ile Cys Pro Gly Tyr Arg Trp Met Cys
            275                 280                 285

Leu Arg Arg Phe Ile Ile Phe Leu Phe Ile Leu Leu Leu Cys Tyr Leu
290                 295                 300

Ile Phe Leu Leu Val Leu Leu Asp Tyr Gln Gly Met Leu Pro Val Cys
305                 310                 315                 320

Pro Leu Ile Leu Pro Gly Ser Thr Thr Thr Asn Thr Gly Pro Cys Lys
                325                 330                 335

Thr Cys Thr Thr Pro Ala Gln Gly Leu Asn Ser Met Phe Pro Ser Cys
                340                 345                 350

Cys Cys Thr Lys Pro Thr Asp Gly Asn Cys Thr Cys Ile Leu Pro Ile
                355                 360                 365

Pro Ser Ser Trp Ala Phe Ala Lys Thr Leu Trp Glu Trp Ala Ser Val
370                 375                 380

Arg Pro His Ser Trp Leu Ser Leu Leu Val Pro Phe Val Gln Trp Phe
385                 390                 395                 400

Val Gly Leu Ser Pro Thr Val Ala Trp Leu Ser Ala Ile Trp Met Met
                405                 410                 415

Trp Tyr Trp Gly Pro Ser Leu Tyr Ser Ile Val Ser Glu Pro Phe Ile
                420                 425                 430

Pro Leu Leu Pro Ile Phe Phe Cys Leu Trp Val Tyr Ile
                435                 440                 445

<210> SEQ ID NO 20
<211> LENGTH: 42
<212> TYPE: DNA
<213> ORGANISM: Unknown
<220> FEATURE:
<223> OTHER INFORMATION: Information relating to cloning site of plasmid
      pGF1-S2 shown in Figure 2

<400> SEQUENCE: 20
atgatggctc ccgggatcct acccgggcct gtgacgaaga tg                             42

<210> SEQ ID NO 21
<211> LENGTH: 10
<212> TYPE: PRT
<213> ORGANISM: Unknown
<220> FEATURE:
<223> OTHER INFORMATION: Information relating to cloning site of plasmid
      pGF1-S2 shown in Figure 2

<400> SEQUENCE: 21

Met Met Ala Pro Gly Pro Val Thr Asn Met
1               5                   10

<210> SEQ ID NO 22
<211> LENGTH: 20
<212> TYPE: DNA
<213> ORGANISM: Human

<400> SEQUENCE: 22
```

```
tccatgacgt tcctgacgtt                                              20

<210> SEQ ID NO 23
<211> LENGTH: 18
<212> TYPE: DNA
<213> ORGANISM: Human

<400> SEQUENCE: 23
tctcccagcg tgcgccat                                                18

<210> SEQ ID NO 24
<211> LENGTH: 30
<212> TYPE: DNA
<213> ORGANISM: Human

<400> SEQUENCE: 24
accgatgacg tcgccggtga cggcaccacg                                   30

<210> SEQ ID NO 25
<211> LENGTH: 24
<212> TYPE: DNA
<213> ORGANISM: Human

<400> SEQUENCE: 25
tcgtcgtttt gtcgttttgt cgtt                                         24

<210> SEQ ID NO 26
<211> LENGTH: 20
<212> TYPE: DNA
<213> ORGANISM: Human

<400> SEQUENCE: 26
tccatgacgt tcctgatgct                                              20

<210> SEQ ID NO 27
<211> LENGTH: 22
<212> TYPE: DNA
<213> ORGANISM: Human

<400> SEQUENCE: 27
tcgacgtttt cggcgcgcgc cg                                           22
```

VACCINES FOR MALARIA

CROSS-REFERENCE TO RELATED APPLICATIONS

This application is a 35 U.S.C. §371 National Phase Entry of International Application No. PCT/EP2007/057296, filed Jul. 16, 2007, which is incorporated herein by reference in its entirety. This application also claims the benefit of the earlier filing date of GB Applications Nos. 0614254.1 filed, Jul. 18, 2006; 0614473.7, filed Jul. 20, 2006; 0614476.0, filed Jul. 20, 2006; and 0615115.3, filed Jul. 28, 2006.

NAMES OF PARTIES TO A JOINT RESEARCH AGREEMENT

GlaxoSmithKline Biologicals S.A., and The United States of America, as represented by the Secretary of the Army, also known as the Walter Reed Army Institute of Research, are parties to a joint research agreement.

BACKGROUND OF THE INVENTION

1. Field of the Invention

The present invention relates to a novel lipoprotein particle, methods for preparing and purifying the same, its use in medicine, particularly in the prevention of malarial infections, compositions/vaccines containing the protein or antibodies against the protein particle such as monoclonal or polyclonal antibodies and use of the same, particularly in therapy.

2. Description of Related Art

Malaria is one of the world's major health problems with more than 2 to 4 million people dying from the disease each year. One of the most prevalent forms of the disease is caused by the protozoan parasite *P. vivax*, which is found in tropical and sub-tropical regions. Interestingly the parasite can complete its mosquito cycle at temperatures as low as 15 degrees Celsius, which has allowed the disease to spread in temperate climates.

One of the most acute forms of the disease is caused by the protozoan parasite, *Plasmodium falciparum* (*P. falciparum*) which is responsible for most of the mortality attributable to malaria.

The life cycle of *Plasmodium* is complex, requiring two hosts, man and mosquito for completion. The infection of man is initiated by the introduction of sporozoites in the saliva of an infected mosquito. The sporozoites migrate to the liver and there infect hepatocytes where they differentiate, via the exoerythrocytic intracellular stage, into the merozoite stage which infects red blood cells (RBC) to initiate cyclical replication in the asexual blood stage. The cycle is completed by the differentiation of a number of merozoites in the RBC into sexual stage gametocytes, which are ingested by the mosquito, where they develop through a series of stages in the midgut to produce sporozoites which migrate to the salivary gland.

Due to the fact that the disease caused by *P. vivax* is rarely lethal, efforts to prevent and treat malaria have been focused on the more deadly form of the disease caused by *Plasmodium falciparum* (*P. falciparum*).

Although the disease caused by *P. vivax* does not usually result in death of the patient, due to the volume of cases, which seems to be increasing, the significant impact on the quality of life of the patient, the increasing reports of the severe incidences of the disease resulting in anemia and death, and the economic impact, an effective vaccination for the disease is still required. Furthermore, a single vaccine able to provide protection against both causes of the disease would be advantageous.

A feature of the *P. vivax* is that some strains are capable of causing delayed infection by remaining latent in the liver before emerging into the peripheral circulation to manifest clinical symptoms. Thus individuals, for example when traveling through an infected area, may be infected and yet may not exhibit symptoms for several months. This has the potential to cause the spread of the disease and for this reason persons traveling to infected areas are not allowed to donate blood for transfusion for a defined period of time after traveling to the infected region.

*P. vivax* malaria infection remains latent within the liver while the parasite is undergoing pre-erthrocytic shizogony. If the parasite is controlled at this stage, before it escapes the liver, no clinical symptoms of the disease, are observed in the patient.

The sporozoite stage of *Plasmodium* has been identified as a potential target of a malaria vaccine. Vaccination with deactivated (irradiated) sporozoite has been shown to induced protection against experimental human malaria (Am. J, Trop. Med. Hyg 24: 297-402, 1975). However, it is has not been possible practically and logistically to manufacture a vaccine for malaria for the general population based on this methodology, employing irradiated sporozoites.

The major surface protein of the sporozoite is known as circumsporozoite protein (CS protein). It is thought to be involved in the motility and invasion of the sporozoite during its passage from the initial site of inoculation by the mosquito into the circulation, where it migrates to the liver.

The CS protein of Plasmodia species is characterized by a central repetitive domain (repeat region) flanked by non-repetitive amino (N-terminus) and carboxy (C-terminus) fragments.

The central domain of *P. vivax* is composed of several blocks of a repeat unit, generally of nine tandem amino acids.

In certain Asian strains, after the central repeat region, an additional sequence of approximately 12 amino acids is present (see SEQ ID No 11). The function of the latter is not known. However, it is hypothesized, by some, that said amino acids may be linked to the delayed onset of clinical symptoms of the disease, although this has not been investigated. It is thought that the N-terminus is characterised by a sequence of 5 amino acids known as region I (see SEQ ID No 1). It is also thought that the C-terminus is characterised by comprising a sequence of 18 amino acids known as region II. The latter contains a cell-adhesive motif, which is highly conserved among all malaria CS protein (see SEQ ID No. 2).

Several groups have proposed subunit vaccines based on the circumsporozoite protein. Two of these vaccines have undergone clinical testing; one is a synthetic peptide, the other is a recombinant protein (Ballou et at Lancet: i 1277 (1987) and Herrington et at Nature 328:257 (1987)). These vaccines were successful in stimulating an anti-sporozoite response. Nonetheless, the magnitude of the response was disappointing, with some vaccinees not making a response at all. Furthermore, the absence of "boosting" of antibody levels after subsequent injections and results of in vitro lymphocyte proliferation assays suggested that T-cells of most of these volunteers did not recognise the immuno-dominant repeat. Nonetheless, one volunteer vaccinated in each study did not develop parasitemia.

WO 93/10152 and WO 98/05355 describe a vaccine derived from the CS protein of *P. falciparum* and it seems that there has been some progress made towards the vaccination against *P. falciparum* using the approach described therein, see also Heppner et al. 2005, Vaccine 23, 2243-50.

The CS protein in *P. falciparum* has a central repeat region that is conserved. In contrast at least two forms (designated VK210 or type I and VK247 or type II) of the CS protein for *P. vivax* are known. This renders it more difficult to identify a construct of the CS protein with all the desired properties such as immogenicity, which provides general protection against *P. vivax* regardless of the specific type of CS protein because antibodies directed the central repeating region of type I do not necessarily recognize epitopes on the corresponding region of type II and vice versa.

A recombinant *P. vivax* CS protein was expressed and tested as a vaccine in the 1980-1990's with limited success (Collins et al., 1989. Am. J. Trop. Med. Hyg. 40, 455-64). Some work has been done to develop a vaccine based on Multiple Antigen Peptides (MAP) employing one or more epitopes that are cross-linked (Nardelli and Tam, 1995, Pharm. Biotechnol. 6, 803-19).

BRIEF SUMMARY OF THE INVENTION

The present invention provides an antigenic particle for use in malaria vaccines, which is believed to produce a humoral response and also a cellular immune response. The antigenic particle is believed to induce the production of antibodies against the CS protein of *P. falciparum* and *P. vivax*, type I and type II. The antigen may also induce T helper cells, for example Th1 and/or Th2 cells.

Accordingly, the present invention provides an immunogenic protein particle comprising the following monomers:
a. a fusion protein comprising sequences derived from a CS protein of *P. vivax* and the S antigen of Hepatitis B (CSV-S), and
b. a fusion protein comprising sequences derived from CS protein of *P. falciparum* and S antigen of Hepatitis B (RTS), and optionally
c. S antigen derived from Hepatitis B virus.

SEQUENCE LISTING

SEQ. ID. No. 1 Region I in the N-terminus
SEQ. ID. No. 2' Region II in the C-terminus
SEQ. ID. No. 3-9 Various repeat units of type I CS protein
SEQ. ID. No. 10 Major repeat unit from type II CS protein
SEQ. ID. No. 11 Additional amino acids found in Asian strains
SEQ. ID. No. 12 Nucleotide sequence of the hybrid protein CSV (optimized for expression in *E Coli*)
SEQ. ID. No. 13 Amino acid sequence of the hybrid protein CSV
SEQ. ID. No. 14 Minor repeat unit from type II CS protein
SEQ. ID. No. 15 Nucleotide sequence for the hybrid protein CSV (optimized for expression in yeast)
SEQ. ID. No. 16 Nucleotide sequence for the hybrid fusion protein CSV-S
SEQ. ID. No. 17 Amino acid sequence for the hybrid fusion protein CSV-S
SEQ. ID No. 18 Nucleotide Sequence for an RTS expression cassette and predicted RTS,S protein.
SEQ. ID. No. 19 Amino acid sequence for a fusion of RTS from the CS protein of *P. falciparum* and S antigen from hepatitis B.
SEQ. ID. No. 20 Cloning site of pGF1-S2.

SEQ. ID. No. 21 Amino acid sequence from SEQ. ID. No. 20.
SEQ. ID/Nos. 22-27 CpG oligonucleotides.

BRIEF DESCRIPTION OF THE SEVERAL VIEWS OF THE DRAWINGS

FIG. 3 Plasmid map of pRIT15582
   Digestion with XhoI liberates a 8.5 kb linear DNA fragment carrying the CSV-S expression cassette plus the LEU2 selective marker, being used for insertion into the yeast chromosome.

FIG. 4 Restriction map of the linear XhoI fragment used to integrate CSV-S cassette FIG. 5 Western blot of recombinant proteins expressed in strain Y1835.
   Panel A: WB revealed with anti-S antibody
      Samples loaded (100 µg total protein/well):
      1: Y1631 (RTS,S producing strain, as comparison)
      2: Y1835
      3: Y1835
      4: Y1834
   Panel B: WB revealed with anti-CSV antibody
      Samples loaded (100 µg total protein/well):
      1: Y1631 (RTS,S producing strain, as comparison)
      2: Y1295
      3: Y1835
      4: Y1834
      5: nr (another construct CSVS)
      6: nr (another construct—S antigen only)

FIG. 6 Electron micrograph of CSV-S,S mixed particles produced in strain Y1835
   CSV-S,S particles were purified from soluble cell extracts (based on RTS,S purification process) and submitted to electron microscopy analysis. Particles were visualized after negative staining with phosphotungstic acid. The scale is equivalent to 100 nm.

FIG. 7 Western blot of recombinant proteins expressed in strain Y1845.
   WB revealed with anti-S antibody
   Quantity of total protein loaded is in brackets
      1: Y1835 (100 µg)
      2: Y1631 (100 µg—RTS,S producing strain, as comparison)
      3: Y1845 (100 µg)
      4: Y1845 (50 µg)
      5: Y1845 (25 µg)

FIG. 8 CsCl density analysis of a cell-free extract prepared from strain Y1845

DETAILED DESCRIPTION OF THE INVENTION

Figure 1:
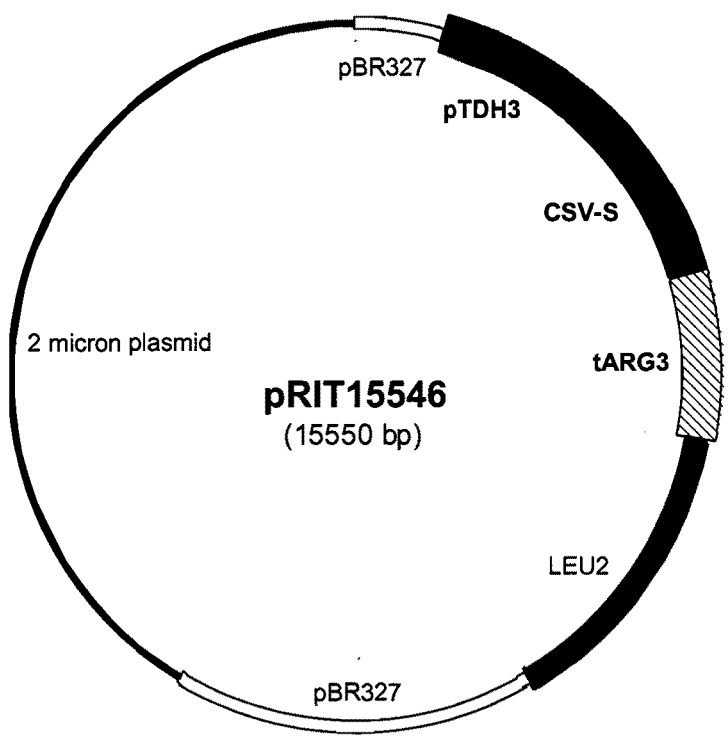
FIG. 1 Plasmid map for pRIT15546 is a yeast episomal vector.

Thus the fusion protein CSV-S employed in the invention comprises: a portion derived from the CS protein of *P. vivax* (CSV). This CSV antigen may a native protein such as found in type I CS proteins of *P. vivax* and/or as found in type II proteins of *P. vivax*. Alternatively the CSV protein may be a hybrid protein or chimeric protein comprising elements from said type I and II CS proteins. When the latter is fused to the S antigen this will be referred to herein as a hybrid fusion protein.

CSV-S is used herein as a generic term to cover fusion proteins comprising a sequence/fragment form the CS protein of *P. vivax* and a sequence/fragment form the S-antigen of Hepatitis B.

RTS is used herein as a generic term to cover fusion proteins comprising a sequence/fragment form the CS protein of *P. falciparum* and a sequence/fragment form the S-antigen of Hepatitis B.

The hybrid/chimeric protein will generally comprise:
at least one repeat unit derived from the central repeat section of a type I circumsporozoite protein of *P. vivax*, and
at least one repeat unit derived from the central repeating section of a type II circumsporozoite protein of *P. vivax*.

Generally the hybrid protein will also contain an N-terminus fragment from CS protein of *Plasmodium* such as *P. vivax*, for example a fragment comprising region I such as the amino acids shown in SEQ ID No. 1.

Usually the hybrid protein will contain a C-terminus fragment from CS protein of *Plasmodium* such as *P. vivax*, for example a fragment comprising region II such as the motif shown in SEQ ID No 2.

Whilst not wishing to be bound by theory it is thought that the N and C terminal fragments include several T and B cell epitopes.

Any suitable strain of *P. vivax* may be employed in the invention including: Latina, America (ie Sal 1, Belem), Korean, China, Thailand, Indonesia, India, and Vietnam. The construct in SEQ ID No 13 is based on a Korean strain (more specifically a South Korean strain).

*P. vivax* with type I CS proteins is more prevalent than *P. vivax* with type II CS proteins. Therefore in one aspect the invention employs a CS protein from type I. In an alternative aspect the invention provides a hybrid protein comprising a repeat unit from type I and a repeat unit from type II, for example wherein more repeat units from type I are included in the hybrid than repeat units of type II.

More specifically the hybrid protein of the invention may include 1 to 15 repeat units such as 9 repeat units from type I.

Examples of suitable repeat units from type I CS proteins are given in SEQ ID No.s 3 to 9.

In one embodiment the invention provides a hybrid with a mixture of different repeat units of type I, such as one of each of those listed in SEQ ID No.s 3 to 9.

One or more repeat units may be duplicated in the hybrid, for example two repeat units of SEQ ID No 3 and/or 4 may be incorporated into the construct.

a) In one aspect the CS protein comprises a unit of SEQ ID No 3.
b) In one aspect the CS protein comprises a unit of SEQ ID No 4, optionally in combination with units as described in paragraph a) directly above.
c) In one aspect the CS protein comprises a unit of SEQ ID No 5, optionally in combination with units as described in paragraph a) or b) directly above.
d) In one aspect the CS protein comprises a unit of SEQ ID No 6, optionally in combination with one or more units as described in paragraphs a) to c) directly above.
f) In one aspect the CS protein comprises a unit of SEQ ID No 7, optionally in combination with one or more units as described in paragraph a) to d) directly above.
g) In one aspect the CS protein comprises a unit of SEQ ID No 8, optionally in combination with one or more units as described in paragraph a) to f) directly above.
h) In one aspect the CS protein comprises a unit of SEQ ID No 9, optionally in combination with one or more units as described in paragraph a) to g) directly above.

Examples of suitable component repeat units from type II CS proteins are given in SEQ ID No.s 10 and 14, such as 10.

In one aspect of the invention there is provided a hybrid protein with 5 or less repeat units derived from type II such as one repeat unit, for example as shown in SEQ ID No. 10.

The hybrid may also include the 12 amino acid insertion found at the end of the repeat region found in certain Asian strains of *P. vivax*, for example as shown in SEQ ID No. 11.

In one embodiment the hybrid protein comprises about 257 amino-acids derived from *P. vivax* CS protein.

The CSV derived antigen component of the invention is generally fused to the amino terminal end of the S protein.

It is believed that the presence of the surface antigen from Hepatitis B boosts the immunogenicity of the CS protein portion, aids stability, and/or assists reproducible manufacturing of the protein.

In one embodiment the hybrid fusion protein comprises about 494 amino acids, for example about 257 of which are derived from *P. vivax* CS protein.

The hybrid fusion protein may also include further antigens derived from *P. falciparium* and/or *P. vivax*, for example wherein the antigen is selected from DBP, PvTRAP, PvMSP2, PvMSP4, PvMSP5, PvMSP6, PvMSP7, PvMSP8, PvMSP9, PvAMA1 and RBP or fragment thereof.

Other example, antigens derived from *P falciparum* include, PfEMP-1, Pfs 16 antigen, MSP-1, MSP-3, LSA-1, LSA-3, AMA-1 and TRAP. Other *Plasmodium* antigens include *P. falciparum* EBA, GLURP, RAPT, RAP2, Sequestrin, Pf332, STARP, SALSA, PfEXP1, Pfs25, Pfs28, PFS27/25, Pfs48/45, Pfs230 and their analogues in other *Plasmodium* spp.

In an embodiment the hybrid fusion protein (CSV-S) has the amino acid sequence shown in SEQ ID No. 17. In the sequence amino acids 6 to 262 are derived from CSV and 269 to 494 are derived from S. The remaining amino acids are introduced by genetic construction (which, in particular may be varied as appropriate). These four amino acids, Met, Met Ala Pro, are derived specifically from plasmid pGF1-S2 (see FIG. 4)

The properties of the CSV-S fusion protein of SEQ ID No. 17 are provided in the Tables below

| Analysis | Whole Protein |
| --- | --- |
| Molecular Weight | 51794.75 m.w. |
| Length | 494 |
| 1 microgram = | 19.307 pMoles |
| Molar Extinction coefficient | 90780 +/− 5% |
| 1 A(280) = | 0.57 mg/ml |
| Isoelectric Point | 7.33 |
| Charge at pH 7 | 1.05 |

| Whole Protein Composition Analysis | | | |
| --- | --- | --- | --- |
| Amino Acid(s) | Number count | % by weight | % by frequency |
| Charged (RKHYCDE) | 106 | 26.35 | 21.46 |
| Acidic (DE) | 38 | 8.82 | 7.69 |
| Basic (KR) | 39 | 10.68 | 7.89 |
| Polar (NCQSTY) | 134 | 28.15 | 27.13 |
| Hydrophobic (AILFWV) | 167 | 34.68 | 33.81 |
| A Ala | 52 | 7.14 | 10.53 |

-continued

Whole Protein Composition Analysis

| Amino Acid(s) | Number count | % by weight | % by frequency |
|---|---|---|---|
| C Cys | 18 | 3.58 | 3.64 |
| D Asp | 24 | 5.33 | 4.86 |
| E Glu | 14 | 3.49 | 2.83 |
| F Phe | 17 | 4.83 | 3.44 |
| G Gly | 64 | 7.05 | 12.96 |
| H His | 4 | 1.06 | 0.81 |
| I Ile | 17 | 3.71 | 3.44 |
| K Lys | 20 | 4.95 | 4.05 |
| L Leu | 42 | 9.18 | 8.50 |
| M Met | 8 | 2.03 | 1.62 |
| N Asn | 32 | 7.05 | 6.48 |
| P Pro | 40 | 7.50 | 8.10 |
| Q Gln | 21 | 5.20 | 4.25 |
| R Arg | 19 | 5.73 | 3.85 |
| S Ser | 30 | 5.04 | 6.07 |
| T Thr | 26 | 5.08 | 5.26 |
| V Val | 25 | 4.78 | 5.06 |
| W Trp | 14 | 5.03 | 2.83 |
| Y Tyr | 7 | 2.21 | 1.42 |
| B Asx | 0 | 0.00 | 0.00 |
| Z Glx | 0 | 0.00 | 0.00 |
| X Xxx | 0 | 0.00 | 0.00 |
| . Ter | 1 | 0.00 | 0.20 |

The nucleotide sequence for protein of SEQ ID No 17 is given in SEQ ID No 16.

The component of the protein particles of the invention termed RTS (ie derived from *P. falciparum*) can be prepared as described in WO 93/10152, which includes a description of the RTS* (from *P. falciparum* NF54/3D7 strain).

In one or more embodiments of the invention the antigen derived from *P. falciparum* employed in the fusion protein may be the substantially the whole CS protein thereof.

In one embodiment of the invention full-length S-antigen is employed. In another embodiment a fragment of said S-antigen is employed.

In one embodiment the antigen derived from of *P. falciparum* comprises at least 4 repeat units the central repeat region. More specifically this antigen comprises a sequence which contains at least 160 amino acids, which is substantially homologous to the C-terminal portion of the CS protein. The CS protein may be devoid of the last 12 to 14 (such as 12) amino-acids from the C terminal.

In particular a fusion protein which comprises a portion of the CS protein of *P. falciparum* substantially as corresponding to amino acids 207-395 of the CS protein of *P. falciparum* (strain NF54[3D7]) 7G8 fused in frame via a linear linker to the N-terminal of the S antigen is employed in the particles. The linker may comprise a portion of preS2 from the S-antigen.

More specifically the fusion protein derived from *P. falciparium* employed is that encoded for by the nucleotide sequence for the RTS expression cassette, provide in SEQ ID No 18.

Suitable S antigens, may comprise a preS2. An example of a suitable serotype is adw (Nature 280:815-819, 1979).

In one aspect the hybrid fusion proteins of the invention comprise a portion derived from a mutant s protein, for example as described in published US application No. 2006/194196 (also published as WO 2004/113369). This document describes a mutant labeled HDB05. In particular it describes comparisons of the mutant and wild type proteins in FIGS. 1 and 6 and genes for the mutant in FIGS. 4 and 5. Sequence 12 to 22 therein describe particular polypeptides of the mutant S protein. Each of the above is incorporated herein by reference.

Figure 2:
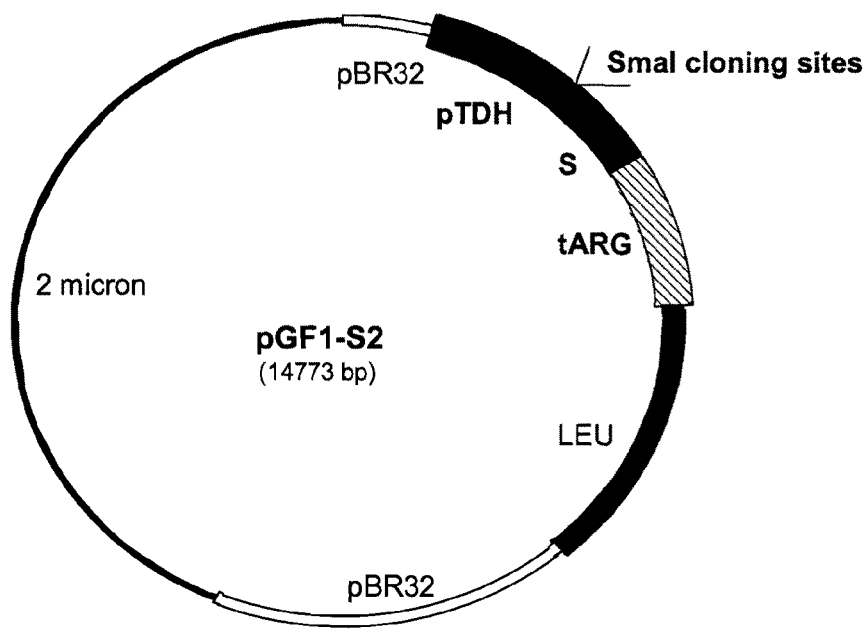
FIG. 2 Plasmid map of pGF1-S2 a plasmid prepared by GSK employed in "fusing" the desired antigen with the S antigen from Hepatitis B. Cloning heterologous DNA sequences between SmaI sites (after excision of the 12 bp SmaI DNA fragment) creates in-frame fusion with the S gene. (SEQ ID NOs. 20 and 21)

The fusion protein CSV-S may for example be prepared employing the plasmid pGF1-S2 (see FIG. 2 and the examples for further details), which when the appropriate sequence corresponding to CSV is inserted at the SmaI cloning site can under suitable conditions produce the fusion protein CSV-S.

The DNA sequences encoding the proteins of the present invention are, in one embodiment flanked by transcriptional control elements, preferably derived from yeast genes and incorporated into an expression vector.

An expression cassette for hybrid proteins of the invention may, for example, be constructed comprising the following features:

A promoter sequence, derived, for example, from the *S. cerevisiae* TDH3 gene.

A sequences encoding for an appropriate fusion protein.

A transcription termination sequence contained within the sequence, derived, for example, from the *S. cerevisiae* ARG3 gene.

An example of a specific promoter is the promoter from the *S. cerevisiae* TDH3 gene Musti et al.

The invention also extends to vectors employed in the preparation of the hybrid fusion protein.

A suitable plasmid can then be employed to insert the sequence encoding for the hybrid fusion protein into a suitable host for synthesis. An example of a suitable plasmid is pRIT15546 a 2 micron-based vector for carrying a suitable expression cassette, see FIG. 1 and Examples for further details.

The plasmid will generally contain an in-built marker to assist selection, for example a gene encoding for antibiotic resistance or LEU2 or HIS auxotrophy.

Generally the host will have an expression cassette for each fusion protein in the particle and may also have one or more expression cassettes for the S antigen integrated in its genome.

The invention also relates to a host cell transformed with a vector according to the invention. Host cells can be prokaryotic or eukaryotic but preferably, are yeast, for example *Saccharomyces* (for example *Saccharomyces cerevisiae* such as DC5 in ATCC data base (accession number 20820), under the name RIT DC5 cir(o). Depositor: Smith Kline-RIT) and non-*Saccharomyces* yeasts. These include *Schizosaccharomyces* (eg *Schizosaccharomyces pombe*) *Kluyveromyces* (eg *Kluyveromyces lactis*), *Pichia* (eg *Pichia pastoris*), *Hansenula* (eg *Hansenula polymorpha*), *Yarrowia* (eg *Yarrowia lipolytica*) and *Schwanniomyces* (eg *Schwanniomyces occidentalis*).

In one aspect the invention relates to a recombinant yeast strain Y1834 (and use thereof), for expressing the fusion protein, see Examples for preparation of the same.

In another embodiment the invention provides a recombinant yeast strain Y1835 or Y1845 (and use of same) for expressing fusion protein of the invention, see Examples for further details.

The nucleotide sequences or part thereof (such as the portion encoding the CS/hybrid protein but optionally not the portion encoding protein S) employed herein may be codon-optimized for expression in a host, such as yeast.

The invention also extends to a host comprising a polynucleotide such as DNA encoding for two or more components of the particle, employed in the present invention.

In one embodiment the host cell comprises an expression cassette for a fusion protein derived from *P. vivax* and an expression cassette for the fusion protein derived from *P. falciparum*.

In certain hosts, such as yeast cells, once expressed the fusion protein (comprising the S antigen) is spontaneously assembled into a protein structure/particle composed of numerous monomers of said fusion proteins. When the yeast expresses two different fusion proteins these are believed to be co-assembled in particles.

When the chosen recipient yeast strain already carries in its genome several integrated copies of Hepatitis B S expression cassettes then the particles assembled may also include monomers of unfused S antigen.

These particles may also be referred to a Virus Like Particles (VLP). The particles may also be described as multimeric lipoprotein particles.

Alternatively these particles can be prepared in a number of ways, for example by fusing each the *Plasmodium* derived antigens to another fusion partner, (for example the antigens of Hepatitis B virus or a viral structural protein) and expressing the same in a suitable host such as yeast or bacteria.

Thus there is provided an immunogenic protein particle comprising the following monomers:

a. a fusion protein comprising sequences derived from a CS protein of *P. vivax*, and
b. a fusion protein comprising sequences derived from CS protein of *P. falciparum.*

In a further aspect the invention provides a fusion protein comprising:

a) a sequence derived from a CS protein of *P vivax* (such as a sequence from the repeat region of type I and/or type II)
b) a sequence derived from the CS protein of *P. falciparum* (such as a sequence from the repeat region thereof), and
c) a sequence from the S-antigen of Hepatitis B.

Thus the invention extends to a protein particle comprising a fusion protein derived from CS protein of *P. vivax* and a fusion protein derived from CS protein of *P. falciparium*, wherein the antigen fused with the *Plasomdium* antigen is chosen to induce the formation/assembly of the lipoparticles when said fusion proteins are expressed in a suitable host.

Thus the invention provides a VLP comprising CSV-S and RTS units. In one aspect the invention provides a particle consisting essentially of CSV-S and RTS units. In an alternative aspect the particles produced comprise or consist of essentially of CSV-S, RTS and S units.

Various approaches can be used to engineer yeast for the preparation of said particles, for example an expression cassette for the fusion protein can be inserted into the genome of a yeast already containing an expression cassette for one of the required fusion proteins and/or the S antigen. However, a skilled person working in the field is well able to prepare a suitable host for the preparation of particles according to the invention.

Thus in one aspect the invention provides a suitable host such as yeast comprising DNA encoding for CSV-S, RTS and optionally S. In an alternative aspect a suitable host is, one or more plasmids capable of expressing CSV-S, RTS and optionally S. The plasmid may, for example be used to express the protein in conjunction with, for example, a yeast.

Whilst not wishing to be bound by theory it is thought that the surfactants used to liberate the protein from the cells may also assist in the stabilization of the lipoprotein particles.

It is hypothesized that the lipoprotein particles of the invention may contribute to further stimulating in vivo the immune response to the antigenic protein(s).

In one aspect the invention provides a replication deficient viral vector encoding a one or more CS proteins, for example which correspond(s) to one or more CS proteins comprised in the particles according the invention.

Suitable viral vectors may be derived from adeno viral vectors, adeno-associated viral vectors (AAVs), measles, lentiviruses, alphaviruses, bacloviruses, herpes simplex virus, and poxviruses such as cowpox, fowlpox, pigeonpox, canarypox, suipox and sheeppox/goatpox. Methodology for preparing adeno viral vectors encoding a malaria antigen is, for example, described in WO 2004/055187.

The protein encoded by the vector may, for example, be modified to prevent glycosylation of the protein during expression, for example certain serines may be replaced by alanine residues to reduce glycosylation.

Viral vectors employed in the invention may be recombinant.

Adenovirus

Adenoviral vectors of the present invention comprise one or more heterologous polynucleotides (DNA) which encode one or more immunogenic polypeptides.

Adenoviral vectors of use in the present invention may be derived from a range of mammalian hosts.

Adenoviruses (herein referred to as "Ad" or "Adv") have a characteristic morphology with an icosahedral capsid consisting of three major proteins, hexon (II), penton base (III) and a knbbed fibre (IV), along with a number of other minor proteins, VI, VIII, IX, Ma and IVa2 (Russell W. C. 2000, Gen Viriol, 81:2573-2604). The virus genome is a linear, double-stranded DNA with a terminal protein attached covalently to the 5' termini, which have inverted terminal repeats (ITRs). The virus DNA is intimately associated with the highly basic protein VII and a small peptide termed mu. Another protein, V, is packaged with this DNA-protein complex and provides a structural link to the capsid via protein VI. The virus also contains a virus-encoded protease, which is necessary for processing of some of the structural proteins to produce mature infectious virus.

Over 100 distinct serotypes of adenovirus have been isolated which infect various mammalian species, 51 of which are of human origin. Thus one or more of the adenoviral vectors may be derived from a human adenovirus. Examples of such human-derived adenoviruses are Ad1, Ad2, Ad4, Ad5, Ad6, Ad11, Ad 24, Ad34, Ad35, Ad50/51 particularly Ad5, Ad11 and Ad35. The human serotypes have been categorised into six subgenera (A-F) based on a number of biological, chemical, immunological and structural criteria.

Although Ad5-based vectors have been used extensively in a number of gene therapy trials, there may be limitations on the use of Ad5 and other group C adenoviral vectors due to preexisting immunity in the general population due to natural infection. Ad5 and other group C members tend to be among the most seroprevalent serotypes. Immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

One such area of alternative serotypes are those derived from non human primates, especially chimpanzee adenoviruses. See U.S. Pat. No. 6,083,716 which describes the genome of two chimpanzee adenoviruses.

It has been shown that chimpanzee ("Pan" or "C") adenoviral vectors induce strong immune responses to transgene products as efficiently as human adenoviral vectors (Fitzgerald et al. J. Immunol. 170:1416).

Non-human primate adenoviruses can be isolated from the mesenteric lymph nodes of chimpanzees. Chimpanzee adenoviruses are sufficiently similar to human adenovirus subtype C to allow replication of E1 deleted virus in HEK 293 cells. Yet chimpanzee adenoviruses are phylogenetically distinct from the more common human serotypes (Ad2 and Ad5). Pan 6 is less closely related to and is serologically distinct from Pans 5, 7 and 9.

Thus one or more of the adenoviral vectors may be derived from a non-human primate adenovirus eg a chimpanzee adenovirus such as one selected from serotypes Pan5, Pan6, Pan7 and Pan9.

Adenoviral vectors may also be derived from more than one adenovirus serotype, and each serotype may be from the same or different source. For example they may be derived from more than one human serotype and/or more than one non-human primate serotype. Methods for constructing chimeric adenoviral vectors are disclosed in WO2005/001103.

There are certain size restrictions associated with inserting heterologous DNA into adenoviruses. Human adenoviruses have the ability to package up to 105% of the wild type genome length (Bett et al 1993, J Virol 67 (10), 5911-21). The lower packaging limit for human adenoviruses has been shown to be 75% of the wild type genome length (Parks et al 1995, J Virol 71(4), 3293-8).

One example of adenoviruses useful in the present invention are adenoviruses which are distinct from prevalent naturally occurring serotypes in the human population such as Ad2 and Ad5. This avoids the induction of potent immune responses against the vector which limits the efficacy of subsequent administrations of the same serotype by blocking vector uptake through neutralizing antibody and influencing toxicity.

Thus, the adenovirus may be an adenovirus which is not a prevalent naturally occurring human virus serotype. Adenoviruses isolated from animals have immunologically distinct capsid, hexon, penton and fibre components but are phylogenetically closely related. Specifically, the virus may be a non-human adenovirus, such as a simian adenovirus and in particular a chimpanzee adenovirus such as Pan 5, 6, 7 or 9. Examples of such strains are described in WO 03/000283 and are available from the American Type Culture Collection, 10801 University Boulevard, Manassas, Va. 20110-2209, and other sources. Desirable chimpanzee adenovirus strains are Pan 5 [ATCC VR-591], Pan 6 [ATCC VR-592], and Pan 7 [ATCC VR-593].

Use of chimpanzee adenoviruses is thought to be advantageous over use of human adenovirus serotypes because of the lack of pre-existing immunity, in particular the lack of cross-neutralising antibodies, to adenoviruses in the target population. Cross-reaction of the chimpanzee adenoviruses with pre-existing neutralizing antibody responses is only present in 2% of the target population compared with 35% in the case of certain candidate human adenovirus vectors. The chimpanzee adenoviruses are distinct from the more common human subtypes Ad2 and Ad5, but are more closely related to human Ad4 of subgroup E, which is not a prevalent subtype. Pan 6 is less closely related to Pan 5, 7 and 9.

The adenovirus of the invention may be replication defective. This means that it has a reduced ability to replicate in non-complementing cells, compared to the wild type virus. This may be brought about by mutating the virus e.g. by deleting a gene involved in replication, for example deletion of the E1a, E1b, E3 or E4 gene.

The adenoviral vectors in accordance with the present invention may be derived from replication defective adenovirus comprising a functional E1 deletion. Thus the adenoviral vectors according to the invention may be replication defective due to the absence of the ability to express adenoviral E1a and E1b, i.e., are functionally deleted in E1a and E1b. The recombinant adenoviruses may also bear functional deletions in other genes [see WO 03/000283] for example, deletions in E3 or E4 genes (or part thereof such as part of E3). The adenovirus delayed early gene E3 may be eliminated from the adenovirus sequence which forms part of the recombinant virus. The function of E3 is not necessary to the production of the recombinant adenovirus particle. Thus, it is unnecessary to replace the function of this gene product in order to package a recombinant adenovirus useful in the invention. In one particular embodiment the recombinant adenoviruses have functionally deleted E1 and E3 genes. The construction of such vectors is described in Roy et al., Human Gene Therapy 15:519-530, 2004. In one aspect the adeno virus has E1 and E4 deleted and part of E3 deleted.

Recombinant adenoviruses may also be constructed having a functional deletion of the E4 gene, although it may be desirable to retain the E4 ORF6 function. Adenovirus vectors according to the invention may also contain a deletion in the delayed early gene E2a. Deletions may also be made in any of the late genes L1 through to L5 of the adenovirus genome. Similarly deletions in the intermediate genes IX and IVa may be useful.

Other deletions may be made in the other structural or non-structural adenovirus genes. The above deletions may be used individually, i.e. an adenovirus sequence for use in the present invention may contain deletions of E1 only. Alternatively, deletions of entire genes or portions thereof effective to destroy their biological activity may be used in any combination. For example in one exemplary vector, the adenovirus sequences may have deletions of the E1 genes and the E4 gene, or of the E1, E2a and E3 genes, or of the E1 and E3 genes (such as functional deletions in E1a and E1b, and a deletion of at least part of E3), or of the E1, E2a and E4 genes, with or without deletion of E3 and so on. Such deletions may be partial or full deletions of these genes and may be used in combination with other mutations, such as temperature sensitive mutations to achieve a desired result.

The adenoviral vectors can be produced on any suitable cell line in which the virus is capable of replication. In particular, complementing cell lines which provide the factors missing from the viral vector that result in its impaired replication characteristics (such as E1 and/or E4) can be used. Without limitation, such a cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources, such as PER.C6© cells, as represented by the cells deposited under ECACC no. 96022940 at the European Collection of Animal Cell Cultures (ECACC) at the Centre for Applied Microbiology and Research (CAMR, UK) or Her 96 cells (Crucell).

The invention extends to use of known cell lines for the preparation of a viral vector encoding a protein of the present invention.

The polynucleotide sequences which encode immunogenic CS polypeptides may be codon optimised for mammalian cells. Such codon-optimisation is described in detail in WO 05/025614.

The present invention also relates to vaccines comprising an immunoprotective amount of protein particle according to the invention in admixture with a suitable diluent or carrier.

The invention also extend to a composition comprising a particle according to the invention and a viral vector comprising a malaria antigen, particularly a malaria antigen common with said particle, and optionally an adjuvant.

In the context of this specification excipient, refers to a component in a pharmaceutical formulation with no therapeutic effect in its own right. A diluent or carrier falls within the definition of an excipient.

Immunogenic in the context of this specification is intended to refer to the ability to illicit an immune response. This response may, for example be when the lipoprotein particle is administered in an appropriate formulation which may include/require a suitable adjuvant. A booster comprising a dose similar or less than the original dose may be required to obtain the required immunogenic response.

The composition/pharmaceutical formulations according to the invention may also include in admixture one or more further antigens such as those derived from *P. falciparium* and/or *P. vivax*, for example wherein the antigen is selected from DBP, PvTRAP, PvMSP2, PvMSP4, PvMSP5, PvMSP6, PvMSP7, PvMSP8, PvMSP9, PvAMA1 and RBP or fragment thereof.

Other example, antigens derived from *P falciparum* include, PfEMP-1, Pfs 16 antigen, MSP-1, MSP-3, LSA-1, LSA-3, AMA-1 and TRAP. Other *Plasmodium* antigens include *P. falciparum* EBA, GLURP, RAPT, RAP2, Sequestrin, Pf332, STARP, SALSA, PfEXP1, Pfs25, Pfs28, PFS27/25, Pfs48/45, Pfs230 and their analogues in other *Plasmodium* spp.

The compositions/pharmaceutical formulations according to the invention may also comprise particles of RTS, S (as described in WO 93/10152) in admixture with the particles according to the invention.

In one embodiment the viral vector construct is as described in WO 2004/055187.

In the vaccine of the invention, an aqueous solution of the particle may be used directly. Alternatively, the protein with or without prior lyophilisation can be mixed or absorbed with any of the known adjuvants which include but are not limited to alum, muramyl dipeptide, saponins such as QUIL A®.

Particular adjuvants are those selected from the group of metal salts, oil in water emulsions, Toll like receptors agonist, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof with the proviso that metal salts are only used in combination with another adjuvant and not alone unless they are formulated in such a way that not more than about 60% of the antigen is adsorbed onto the metal salt. More specifically, not more than about 50%, for example 40% of the antigen is adsorbed onto the metal salt, and in one embodiment not more than about 30% of the antigen is adsorbed onto the metal salt. The level of antibody adsorbed onto the metal salt may be determined by techniques well known in the art. The level of free antigen may be increased by, for example, formulating the composition in the presence of phosphate ions, such as phosphate buffered saline, or by increasing the ratio of antigen to metal salt. In one embodiment the adjuvant does not include a metal salt as sole adjuvant. In one embodiment the adjuvant does not include a metal salt.

In an embodiment the adjuvant is a Toll like receptor (TLR) 4 ligand, preferably an agonist such as a lipid A derivative particularly monophosphoryl lipid A or more particularly 3 Deacylated monophoshoryl lipid A (3D-MPL).

3 Deacylated monophosphoryl lipid A is known from U.S. Pat. No. 4,912,094 and UK patent application No. 2,220,211 (Ribi) and is available from Ribi Immunochem, Montana, USA.

3D-MPL is sold under the trademark MPL® by Corixa corporation and primarily promotes CD4+ T cell responses with an IFN-g (Th1) phenotype. It can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3D-MPL is used. Small particle 3D-MPL has a particle size such that it may be sterile-filtered through a 0.22 µm filter. Such preparations are described in International Patent Application No. WO 94/21292. Synthetic derivatives of lipid A are known and thought to be TLR 4 agonists including, but not limited to:

OM174 (2-deoxy-6-O-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S,9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-,9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127).

Typically when 3D-MPL is used the antigen and 3D-MPL are delivered with alum or presented in an oil in water emulsion or multiple oil in water emulsions. The incorporation of 3D-MPL is advantageous since it is a stimulator of effector T-cells responses.

Other TLR4 ligands which may be used are alkyl Glucosaminide phosphates (AGPs) such as those disclosed in WO 9850399 or U.S. Pat. No. 6,303,347 (processes for preparation of AGPs are also disclosed), or pharmaceutically acceptable salts of AGPs as disclosed in U.S. Pat. No. 6,764, 840. Some AGPs are TLR4 agonists, and some are TLR4 antagonists. Both are thought to be useful as adjuvants.

Another immunostimulant for use in the present invention is QUIL A® and its derivatives. QUIL A® is a saponin preparation isolated from the South American tree *Quilaja Saponaria Molina* and was first described as having adjuvant activity by Dalsgaard et al. in 1974 ("Saponin adjuvants", Archiv. für die gesamte Virusforschung, Vol. 44, Springer Verlag, Berlin, p 243-254). Purified fragments of QUIL A® have been isolated by HPLC which retain adjuvant activity without the toxicity associated with QUIL A® (EP 0 362 278), for example QS7 and QS21 (also known as QA7 and QA21). QS-21 is a natural saponin derived from the bark of *Quillaja saponaria* Molina which induces CD8+ cytotoxic T cells (CTLs), Th1 cells and a predominant IgG2a antibody response.

Particular formulations of QS21 have been described which further comprise a sterol (WO 96/33739). The ratio of QS21:sterol will typically be in the order of 1:100 to 1:1 weight to weight. Generally an excess of sterol is present, the ratio of QS21:sterol being at least 1:2 w/w. Typically for human administration QS21 and sterol will be present in a vaccine in the range of about 1 µg to about 100 µg, such as about 10 µg to about 50 µg per dose.

The liposomes generally contain a neutral lipid, for example phosphatidylcholine, which is usually non-crystalline at room temperature, for example eggyolk phosphatidylcholine, dioleoyl phosphatidylcholine or dilauryl phosphatidylcholine. The liposomes may also contain a charged lipid which increases the stability of the lipsome-QS21 structure for liposomes composed of saturated lipids. In these cases the amount of charged lipid is often 1-20% w/w, such as 5-10%. The ratio of sterol to phospholipid is 1-50% (mol/mol), such as 20-25%.

These compositions may contain MPL (3-deacylated mono-phosphoryl lipid A, also known as 3D-MPL). 3D-MPL is known from GB 2 220 211 (Ribi) as a mixture of 3 types of De-O-acylated monophosphoryl lipid A with 4, 5 or 6 acylated chains and is manufactured by Ribi Immunochem, Montana.

The saponins may be separate in the form of micelles, mixed micelles (generally, but not exclusively with bile salts) or may be in the form of ISCOM matrices (EP 0 109 942), liposomes or related colloidal structures such as worm-like or ring-like multimeric complexes or lipidic/layered structures and lamellae when formulated with cholesterol and lipid, or in the form of an oil in water emulsion (for example as in WO 95/17210). The saponins may often be associated with a metallic salt, such as aluminium hydroxide or aluminium phosphate (WO 98/15287).

Usually, the saponin is presented in the form of a liposome, ISCOM or an oil in water emulsion.

Immunostimulatory oligonucleotides may also be used. Examples oligonucleotides for use in adjuvants or vaccines of the present invention include CpG containing oligonucleotides, generally containing two or more dinucleotide CpG motifs separated by at least three, more preferably at least six or more nucleotides. A CpG motif is a Cytosine nucleotide followed by a Guanine nucleotide. The CpG oligonucleotides are typically deoxynucleotides. In one embodiment the internucleotide in the oligonucleotide is phosphorodithioate, or more preferably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. No. 5,666,153, U.S. Pat. No. 5,278,302 and WO 95/26204.

Examples of oligonucleotides are as follows:

```
TCC ATG ACG TTC CTG ACG TT (CpG 1826)

TCT CCC AGC GTG CGC CAT (CpG 1758)

ACC GAT GAC GTC GCC GGT GAC GGC ACC ACG

TCG TCG TTT TGT CGT TTT GTC GTT (CpG 2006)

TCC ATG ACG TTC CTG ATG CT (CpG 1668)

TCG ACG TTT TCG GCG CGC GCC G (CpG 5456),
``` the sequences may contain phosphorothioate modified internucleotide linkages.

Alternative CpG oligonucleotides may comprise one or more sequences above in that they have inconsequential deletions or additions thereto.

The CpG oligonucleotides may be synthesized by any method known in the art (for example see EP 468520). Conveniently, such oligonucleotides may be synthesized utilising an automated synthesizer.

Examples of a TLR 2 agonist include peptidoglycan or lipoprotein. Imidazoquinolines, such as Imiquimod and Resiquimod are known TLR7 agonists. Single stranded RNA is also a known TLR agonist (TLR8 in humans and TLR7 in mice), whereas double stranded RNA and poly IC (polyinosinic-polycytidylic acid—a commercial synthetic mimetic of viral RNA) are exemplary of TLR 3 agonists. 3D-MPL is an example of a TLR4 agonist whilst CpG is an example of a TLR9 agonist.

An immunostimulant may alternatively or in addition be included. In a one embodiment this immunostimulant will be 3 Deacylated monophosphoryl lipid A (3D-MPL).

In one aspect the adjuvant comprises 3D-MPL.

In one aspect the adjuvant comprises QS21.

In one aspect the adjuvant comprises CpG.

In one aspect the adjuvant is formulated as an oil in water emulsion.

In one aspect the adjuvant is formulated as liposomes.

Adjuvants combinations include 3D-MPL and QS21 (EP 0 671 948 B1), oil in water emulsions comprising 3D-MPL and QS21 (WO 95/17210, WO 98/56414), or 3D-MPL formulated with other carriers (EP 0 689 454 B1). Other preferred adjuvant systems comprise a combination of 3D-MPL, QS21 and a CpG oligonucleotide as described in U.S. Pat. No. 6,558,670 and U.S. Pat. No. 6,544,518.

In one embodiment of the present invention provides a vaccine comprising a particle as herein described, in combination with 3D-MPL and a carrier. Typically the carrier will be an oil in water emulsion or alum.

The protein particles of the present invention may also be encapsulated into microparticles such as liposomes.

Vaccine preparation is generally described in New Trends and Developments in Vaccines, edited by Voller et al., University Park Press, Baltimore, Md., U.S.A., 1978.

Encapsulation within liposomes is described, for example, by Fullerton, U.S. Pat. No. 4,235,877.

The amount of the protein particles of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each does will comprise 1-1000 µg of protein, preferably 1-200 µg most preferably 10-100 µg. An optimal amount for a particular vaccine can be ascertained by standard studies involving observation of antibody titres and other responses in subjects. Following an initial vaccination, subjects will preferably receive a boost in about 4 weeks, followed by repeated boosts every six months for as long as a risk of infection exists. The immune response to the protein of this invention is enhanced by the use of adjuvant and or an immuno stimulant.

The amount of 3D MPL used is generally small, but depending on the vaccine formulation may be in the region of 1-1000 µg per dose, for example 1-500 µg per dose, and such as between 1 to 100 µg per dose.

The amount of CpG or immunostimulatory oligonucleotides in the adjuvants or vaccines of the present invention is generally small, but depending on the vaccine formulation may be in the region of 1-1000 µg per dose, preferably 1-500 µg per dose, and more preferably between 1 to 100 µg per dose.

The amount of saponin for use in the adjuvants of the present invention may be in the region of 1-1000 µg per dose, preferably 1-500 µg per dose, more preferably 1-250 µg per dose, and most preferably between 1 to 100 µg per dose.

The formulations of the present invention may be used for both prophylactic and therapeutic purposes. Therapy includes prophylactic treatment. Accordingly the invention provides a vaccine composition as described herein for use in medicine, for example, for the treatment (including phrophylaxis) of malaria.

A further aspect of the present invention is to provide a process for the preparation of hybrid protein of the invention, which process comprises expressing DNA sequence encoding the protein, in a suitable host, preferably a yeast, and recovering the product.

A further aspect of the invention lies in a method of treating a patient susceptible to *plasmodium* infections by administering an effective amount of a vaccine as hereinbefore described.

In a further aspect there is provided a combination for treatment comprising:
an immunogenic particle according to the invention an a viral vector encoding for a malaria antigen, such as said hybrid antigen.

For example wherein said particle and said viral vector are administered concomitantly, for example they may be admixed for administration simultaneously or alternatively may formulated for administration sequentially.

As used herein the term "concomitantly" means wherein said combination of components are administered within a period of no more than 12 hours eg within a period of no more than 1 hour, typically on one occasion e.g. in the course of the same visit to the health professional, for example where they are administered sequentially or simultaneously.

The invention also includes prime boost regimes with the various components described herein, for example priming with viral vector and boosting with said particles or vice versa.

In the context of this specification comprising is to be interpreted as including.

Aspects of the invention comprising a certain element are also intended to extend to said aspects consisting or consisting essentially of the relevant elements.

The examples below are shown to illustrate the methodology, which may be employed to prepare particles of the invention. The examples may or may not form an aspect of the invention.

EXAMPLES

Example 1

Description of Strain Y1834

The yeast recombinant strain Y1834 may be used to express the fusion protein. It consists of the *Saccharomyces cerevisiae* host strain DC5 transformed with the recombinant expression vector pRIT15546.

DC5 is a laboratory yeast strain (ATCC No: 20820) with the following genotype: leu2-3, leu2-112, his3, can1-11. The double leu-2 mutation permits selection for the uptake and maintenance of the pRIT15546 vector which carries a functional LEU-2 gene copy. Only those cells carrying a vector with a LEU-2 gene can grow when leucine is absent from the growth medium.

The vector pRIT15546 is a yeast episomal expression vector (2μ-based vector) carrying the expression cassette. The recombinant expression is driven by a promoter derived from the yeast TDH3 gene (constitutive expression). The construction of pRIT15546 vector is detailed below.

Construction of pRIT15546 vector.

A synthetic gene, with an appropriate codon usage for yeast expression is constructed and sub-cloned into pUC57 vector. The resulting plasmid pUC57/CSV and the yeast expression vector pGf1-S2 are both restricted with the appropriate enzyme. The vector pGf1-S2 was constructed (at GSK) by a multistep cloning procedure. This vector, which already carries an S expression cassette, allows the construction of fusion genes, as N-terminal in-frame fusion with the S gene of Hepatitis B virus. The final expression vector, after sequence verification, was named pRIT15546 (FIG. 3)

Transformation of strain DC5.

The leu- and his-auxotrophic DC5 strain is transformed with the recombinant plasmid pRIT15546, by using yeast standard protocol. Transformed cells were plated on agar selective plates. One transformant was selected and received the official designation Y1834.

Expression of the Recombinant Protein:

Y1834 is grown, at 30° C., in YNB (Yeast Nitrogen Base available from Kracker Scientific Inc) minimal medium supplemented with 8 μg/ml histidine to an O.D. (620 nm) of 0.5. Then cells are harvested and cellular extracts are prepared.

Extract Preparation:

Cells are resuspended in Breaking Buffer and mechanically disrupted (glass beads). Extract is centrifuged for 15 minutes at 5000 rpm. Supernatant fraction is run on SDS-PAGE 4-20%.

Breaking Buffer: 50 mM phosphate Na buffer (PH: 7.5)
   4mMEDTA
   TWEEN™-20 0.5%
   +proteases inhibitor cocktail (COMPLETE™/ROCHE)

Cell concentration: 100 ml culture (OD: 0.5) in 5 ml breaking buffer=concentration of 10 OD unit/ml.

Crude extract clarification: extract centrifuged 15 minutes/ 5000 rpm

Detection of Recombinant Protein

Clarified extracts are run on SDS-PAGE 4-20%, proteins transferred to nitrocellulose membrane and subjected to immunostaining Western blot analysis:

Reagent=Mouse monoclonal antibody anti-S (prepared by GSK Biologicals)—(dilution: 1/500)

Anti-S antibodies which are commercially available may be substituted for those employed in this method. Alternatively anti-CSV antibodies may be employed, for example those known as MR4 available from NIH.

Example 2

Description of Strain Y1835

The yeast recombinant strain Y1835 simultaneously expresses the CSV-S fusion protein and the S antigen. To obtain a strain co-expressing CSV-S and S proteins, the *Saccharomyces cerevisiae* strain Y1295, which already carries five integrated copies of S expression cassettes, was transformed with the recombinant integrative expression vector pRIT15582.

The strain Y1295 was constructed at GSK by a multistep transformation procedure. The construction of Y1295 strain is described in WO 93/10152. Strain Y1295 has the following genotype: leu2-3, leu2-112, gal1. The leu-2 mutation permits selection for the uptake of pRIT15582-derived linear DNA fragment which carries the CSV-S cassette and the functional LEU2 gene.

The vector pRIT15582 is a yeast integrative expression vector (Ty-based vector) carrying the CSV-S expression cassette. The recombinant expression is driven by a promoter derived from the yeast TDH3 gene (constitutive expression). The construction of pRIT15582 vector is detailed below.

Construction of pRIT15582 integrative vector.

The starting material used to construct pRIT15582 vector was the expression plasmid pRIT15546 (FIG. 1). The construction of this plasmid is described in example 1. Digestion of pRIT 15546 with HindIII endonuclease liberates a 3706 bp long DNA fragment corresponding to the complete CSV-S expression cassette (pTDH3+CSV-S+tARG3). This HindIII DNA fragment (after filling with T4 DNA polymerase) was inserted on the Ty-based integrative vector pRIT13144 at the unique SalI cloning site (SalI restricted/T4 treated). The resulting plasmid pRIT15582 contains, in addition to the expression cassette, the yeast LEU2 gene as selective marker (FIG. 3). Digestion of pRIT15582 with XhoI endonuclease liberates a 8500 bp linear fragment shown in FIG. 4 which can be integrated into the yeast genome by homologous recombination of the free ends with resident Ty elements.

Transformation of strain Y1295.

To obtain a strain expressing both S and CSV-S proteins, strain Y1295 was transformed with the 8500 bp linear XhoI fragment (FIG. 4) with selection for Leu+ colonies. Several integrants containing sets of both expression cassettes present in the genome at various ratio were obtained. One transformant carrying four copies of CSV-S cassettes was selected and given the official designation Y1835.

Expression of the Recombinant Protein:

Y1835 is grown, at 30° C., in YNB (Yeast Nitrogen Base available from Kracker Scientific Inc) minimal medium to an O.D (620 nm) of about 0.5 (0.8). Then cells are harvested and cellular extracts are prepared.

Analysis of Expression Products by Immunoblotting:

Extract Preparation:

Cells are re-suspended in Breaking Buffer and mechanically disrupted (glass beads). Extract is centrifuged for 5-10 minutes at 5000 rpm. Supernatant fraction is run on SDS-PAGE 12.5%.

Breaking Buffer: 50 mM phosphate Na buffer (PH: 7.5)
  4mMEDTA
  TWEEN™-20 0.5%
  +proteases inhibitor cocktail (COMPLETE™/ROCHE)
Cell concentration: 100 ml culture (OD: 0.5) in 2.5 ml breaking buffer=concentration of 20 OD unit/ml.
Crude extract clarification: extract centrifuged 5-10 minutes/5000 rpm
Detection of Recombinant Protein
  Clarified extracts are run on SDS-PAGE 12.5%, proteins transferred to nitrocellulose membrane and subjected to immunostaining
  Western blot analysis (FIG. 5):
  Reagents: 1/Mouse monoclonal antibody anti-S (prepared by GSK Biologicals)—(dilution: 1/250)
    2/Rabbit polyclonal antibody anti-CSV (kindly provided by WRAIR)—dilution 1/20,000.
  Anti-S antibodies as well as anti-*P. vivax*/CSP antibodies which are commercially available may be substituted for those employed in this method.

Example 3

Description of Strain Y1845

The yeast recombinant strain Y1845 simultaneously expresses the CSV-S fusion protein, the RTS fusion and the S antigen. To obtain a strain co-expressing CSV-S, RTS and S proteins, the *Saccharomyces cerevisiae* strain Y1295, which already carries five integrated copies of S expression cassettes, was transformed with an equimolar solution of RTS and CSV-S linear DNA fragments derived from pRIT13540 and pRIT15582 integrative vector, respectively.

The strain Y1295 was constructed at GSK by a multistep transformation procedure. The construction of Y1295 strain is described in WO 093/10152 file. Strain Y1295 has the following genotype: leu2-3, leu2-112, gall. The leu-2 mutation permits selection for the uptake of pRIT15582-derived linear DNA fragment which carries the CSV-S cassette and the functional LEU2 gene.

The vectors pRIT13540 and pRIT15582 are yeast integrative expression vectors (Ty-based vector) carrying the RTS and CSV-S expression cassettes, respectively. For both vectors, the recombinant expression is driven by a promoter derived from the yeast TDH3 gene (constitutive expression). The construction of pRIT15582 vector is detailed in example 2. The construction of pRIT13540 vector is described in WO 93/10152 file.

Preparation of the linear integrative DNA fragments.

The integrative vectors pRIT13540 and pRIT15582 were both restricted with XhoI endonuclease, liberating a 8200 bp and a 8500 bp DNA fragments, respectively. These fragments can be integrated into the yeast genome by homologous recombination of the free ends with resident Ty elements.

Transformation of strain Y1295.

To obtain a strain expressing the three RTS, CSV-S and S proteins, strain Y1295 was transformed with an equimolar solution of the 8200 bp and the 8500 bp linear XhoI fragments, with selection for Leu+ colonies. Several integrants containing sets of the two expression cassettes present in the genome at various ratio were obtained. One transformant carrying four copies of CSV-S, and two copies of RTS (in addition to the five copies of S cassettes) was selected and given the official designation Y1845.

Expression of the Recombinant Protein:

Y1845 is grown, at 30° C., in YNB (Yeast Nitrogen Base available from Kracker Scientific Inc) minimal medium to an O.D. (620 nm) of 0.5. Then cells are harvested and cellular extracts are prepared.

Analysis of Expression Products by Immunoblotting:

Extract Preparation:

Cells are re-suspended in Breaking Buffer and mechanically disrupted (glass beads). Extract is centrifuged for 5-10 minutes at 5000 rpm. Supernatant fraction is run on SDS-PAGE 12.5%.

Breaking Buffer: 50 mM phosphate Na buffer (PH: 7.5)

4mMEDTA

TWEEN™-20 0.5%

+proteases inhibitor cocktail (COMPLETE™/ROCHE)

Cell concentration: 100 ml culture (OD: 0.5) in 5 ml breaking buffer=concentration of 10 OD unit/ml.

Crude extract clarification: extract centrifuged 5-10 minutes/5000 rpm

Detection of Recombinant Protein

Clarified extracts are run on SDS-PAGE 12.5%, proteins transferred to nitrocellulose membrane and subjected to immunostaining Western blot analysis:
Reagent: Mouse monoclonal antibody anti-S (prepared by GSK Biologicals)—(dilution: 1/500)

CsCl Density Gradient Centrigugation:

The formation of particles in strain Y1845 was analyzed by CsCl density gradient centrifugation. Crude extracts (~20 mg of total protein) was analyzed on a 12 ml 1.5 M CsCl gradient (88 hours at 40.000 rpm, +8° C. in a Beckman 70.1 Ti rotor). Fractions (~0.6 ml) were collected and analyzed by immunoblot using an anti-S antibody. As shown in FIG. 8 western blots peaks appear at the same fractions (No. 10 and 11) of the gradient corresponding to a buoyant density of 1.21 and 1.20 g/cm3. The triple particle formation is supported by gradient analysis.

The invention claimed is:

1. An immunogenic protein particle comprising:
   (i) a fusion protein comprising a *Plasmodium vivax* circumsporozoite (CS) protein comprising the amino acid sequence of any one or more of SEQ ID numbers 1, 3-11 and 14 and the S antigen of Hepatitis B;
   (ii) an RTS fusion protein comprising a *Plasmodium falciparum* circumsporozoite (CS) protein sequence and the S antigen of Hepatitis B, wherein the RTS fusion protein comprises:
      (a) the polypeptide of SEQ ID NO: 19; or
      (b) a sequence of at least 160 amino acids of the C-terminal portion of the *P. falciparum* CS protein comprising at least four repeat units of the central repeat region of the *P. falciparum* CS protein; and
   (iii) optionally the S antigen of hepatitis B.

2. The immunogenic protein particle of claim 1, wherein the S antigen of Hepatitis B is from serotype adw.

3. The immunogenic protein particle of claim 1, wherein the fusion protein comprising the *P. vivax* CS protein comprises the amino acid sequence of SEQ ID NO: 13.

4. The immunogenic protein particle of claim 1, wherein the fusion protein comprising the *P. vivax* CS protein and the S antigen of Hepatitis B comprises the amino acid sequence of SEQ ID NO: 17.

5. A composition comprising the immunogenic protein particle of claim 1.

6. The composition of claim 5 comprising an adjuvant.

7. The composition of claim 6, wherein the adjuvant is saponin, 3D-MPL, QS21, or a CpG oligonucleotide.

8. The composition of claim 6, wherein the adjuvant comprises QS21 and 3D-MPL.

9. The composition of claim 8, wherein the adjuvant is an oil-in-water emulsion comprising 3D-MPL and QS21.

10. The composition of claim 6, wherein the QS21 is presented in the form of a liposome.

11. The composition of claim 5 further comprising one or more further antigens of *P. falciparum* and/or *P. vivax*.

12. The composition of claim 6, wherein the composition is for parenteral use.

13. A method of eliciting an immune response in a subject comprising administering to the subject an effective amount of the composition of claim 5.

\* \* \* \* \*